United States Patent
Semingson et al.

(10) Patent No.: US 11,464,552 B2
(45) Date of Patent: Oct. 11, 2022

(54) BONE TIE AND BONE TIE INSERTER

(71) Applicant: Spinal Elements, Inc., Carlsbad, CA (US)

(72) Inventors: Taylor Semingson, San Diego, CA (US); Eugene Shoshtaev, Del Mar, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 114 days.

(21) Appl. No.: 16/751,883

(22) Filed: Jan. 24, 2020

(65) Prior Publication Data
US 2020/0367945 A1 Nov. 26, 2020

Related U.S. Application Data

(60) Provisional application No. 62/851,410, filed on May 22, 2019.

(51) Int. Cl.
*A61B 17/70* (2006.01)
*A61B 90/00* (2016.01)

(52) U.S. Cl.
CPC .......... *A61B 17/7074* (2013.01); *A61B 90/39* (2016.02); *A61B 2017/7073* (2013.01); *A61B 2090/3966* (2016.02)

(58) Field of Classification Search
CPC . A61B 17/70; A61B 17/7026; A61B 17/7029; A61B 17/7031; A61B 17/7053;
(Continued)

(56) References Cited

U.S. PATENT DOCUMENTS

| 86,016 A | 1/1869 | Howell |
| 1,630,239 A | 5/1927 | Binkley et al. |

(Continued)

FOREIGN PATENT DOCUMENTS

| CA | 2 437 575 | 4/2009 |
| DE | 93 04 368 | 5/1993 |

(Continued)

OTHER PUBLICATIONS

International Search Report and Written Opinion in International Application No. PCT/US2020/014985, dated Apr. 24, 2020.
(Continued)

*Primary Examiner* — Eduardo C Robert
*Assistant Examiner* — Michelle C Eckman
(74) *Attorney, Agent, or Firm* — Knobbe, Martens, Olson & Bear, LLP

(57) ABSTRACT

Various embodiments of bone ties, bone tie inserters, and methods for treating the spine are provided. The bone tie can include a proximal end and a distal end. The bone tie can include a head section comprising a rounded head. The bone tie can include a neck section extending proximally from the head section. A bone tie inserter for placing a bone tie can also be provided. The bone tie inserter can include a bone tie advancer with a curved surface configured to guide a rounded head of a bone tie. The bone tie inserter can include a bone tie retriever configured to receive the rounded head of a bone tie. The bone tie is configured to pivot and/or rotate within the retriever portion of the bone tie inserter. The method can include forming a lumen in a first bone portion and a second bone portion. The bone tie can be configured to pivot and/or rotate as the bone tie retriever is withdrawn.

18 Claims, 21 Drawing Sheets

(58) Field of Classification Search
CPC .... A61B 17/7062–707; A61B 17/7074; A61B 17/7077; A61B 17/842; A61B 17/8872; A61B 17/8869; A61B 17/82; A61B 17/823; A61B 17/826; Y10T 24/1498; B65D 63/1018; B65D 63/1027
See application file for complete search history.

(56) References Cited

U.S. PATENT DOCUMENTS

| | | |
|---|---|---|
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 2,967,282 A | 1/1961 | Schwartz et al. |
| 3,111,945 A | 11/1963 | Von Solbrig |
| 3,149,808 A | 9/1964 | Weckesser |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,166,292 A | 9/1979 | Bokros |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,570,618 A * | 2/1986 | Wu ........................ A61B 17/707 606/263 |
| 4,573,458 A | 3/1986 | Lower |
| 4,573,459 A | 3/1986 | Litton |
| 4,634,445 A | 1/1987 | Helal |
| 4,643,178 A * | 2/1987 | Nastari ............ A61B 17/06166 606/103 |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,880,429 A | 11/1989 | Stone |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,955,913 A * | 9/1990 | Robinson ................ A61L 31/06 606/228 |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,092,868 A | 3/1992 | Mehdian |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,304,178 A * | 4/1994 | Stahurski ............... A61B 17/82 606/263 |
| 5,306,275 A | 4/1994 | Bryan |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,142 A | 3/1996 | Fodor et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,698 A * | 7/1996 | Preissman ............... A61B 17/82 606/103 |
| 5,540,703 A * | 7/1996 | Barker, Jr. ......... A61B 17/7062 289/1.2 |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,609,634 A | 3/1997 | Voydeville |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |

(56) References Cited

U.S. PATENT DOCUMENTS

| | | | |
|---|---|---|---|
| 5,725,582 A * | 3/1998 | Bevan | A61B 17/7076 606/263 |
| 5,741,260 A | 4/1998 | Songer et al. | |
| 5,741,261 A | 4/1998 | Moskovitz et al. | |
| D395,138 S | 6/1998 | Ohata | |
| 5,766,251 A | 6/1998 | Koshino | |
| 5,766,253 A | 6/1998 | Brosnahan | |
| 5,772,663 A | 6/1998 | Whiteside et al. | |
| 5,797,916 A | 8/1998 | McDowell | |
| 5,810,854 A * | 9/1998 | Beach | A61B 17/0401 24/16 PB |
| 5,824,093 A | 10/1998 | Ray et al. | |
| 5,824,094 A | 10/1998 | Serhan et al. | |
| 5,836,948 A | 11/1998 | Zucherman et al. | |
| 5,851,208 A | 12/1998 | Trott | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,879,396 A | 3/1999 | Walston et al. | |
| 5,888,203 A | 3/1999 | Goldberg | |
| 5,893,889 A | 4/1999 | Harrington | |
| 5,895,428 A | 4/1999 | Berry | |
| RE36,221 E | 6/1999 | Breard et al. | |
| 5,918,604 A | 7/1999 | Whelan | |
| 5,951,555 A | 9/1999 | Rehak et al. | |
| 5,964,765 A | 10/1999 | Fenton et al. | |
| 5,993,452 A | 11/1999 | Vandewalle | |
| 5,997,542 A | 12/1999 | Burke | |
| 6,001,130 A | 12/1999 | Bryan et al. | |
| 6,014,588 A | 1/2000 | Fitz | |
| 6,019,763 A | 2/2000 | Nakamura et al. | |
| 6,019,768 A | 2/2000 | Wenstrom, Jr. et al. | |
| 6,019,792 A | 2/2000 | Cauthen | |
| 6,039,763 A | 3/2000 | Shelokov | |
| 6,048,342 A | 4/2000 | Zucherman et al. | |
| 6,050,998 A | 4/2000 | Fletcher | |
| 6,063,121 A | 5/2000 | Xavier et al. | |
| 6,066,325 A | 5/2000 | Wallace et al. | |
| 6,068,630 A | 5/2000 | Zucherman et al. | |
| RE36,758 E | 6/2000 | Fitz | |
| 6,080,157 A | 6/2000 | Cathro et al. | |
| 6,099,531 A | 8/2000 | Bonutti | |
| 6,102,347 A | 8/2000 | Benoit | |
| 6,106,558 A | 8/2000 | Picha | |
| 6,113,637 A | 9/2000 | Gill et al. | |
| 6,132,464 A | 10/2000 | Martin | |
| 6,132,465 A | 10/2000 | Ray et al. | |
| 6,146,422 A | 11/2000 | Lawson | |
| 6,156,067 A | 12/2000 | Bryan et al. | |
| 6,179,839 B1 | 1/2001 | Weiss et al. | |
| D439,340 S | 3/2001 | Michelson | |
| 6,200,322 B1 | 3/2001 | Branch et al. | |
| 6,293,949 B1 | 9/2001 | Justis et al. | |
| D450,122 S | 11/2001 | Michelson | |
| 6,325,803 B1 | 12/2001 | Schumacher et al. | |
| D454,953 S | 3/2002 | Michelson | |
| 6,368,325 B1 | 4/2002 | McKinley et al. | |
| 6,368,350 B1 | 4/2002 | Erickson et al. | |
| 6,371,958 B1 | 4/2002 | Overaker | |
| 6,375,573 B2 | 4/2002 | Romano | |
| 6,379,386 B1 | 4/2002 | Resch et al. | |
| 6,409,765 B1 | 6/2002 | Bianchi et al. | |
| D460,188 S | 7/2002 | Michelson | |
| D460,189 S | 7/2002 | Michelson | |
| 6,419,678 B1 | 7/2002 | Asfora | |
| 6,419,703 B1 | 7/2002 | Fallin et al. | |
| 6,423,071 B1 * | 7/2002 | Lawson | A61B 17/0469 606/103 |
| 6,436,099 B1 | 8/2002 | Drewry et al. | |
| 6,436,101 B1 | 8/2002 | Hamada et al. | |
| 6,436,146 B1 | 8/2002 | Hassler et al. | |
| D463,560 S | 9/2002 | Michelson | |
| 6,447,544 B1 | 9/2002 | Michelson | |
| 6,470,207 B1 | 10/2002 | Simon et al. | |
| 6,475,220 B1 * | 11/2002 | Whiteside | A61B 17/82 606/224 |
| 6,565,605 B2 | 5/2003 | Goble et al. | |
| 6,572,617 B1 | 6/2003 | Senegas | |
| 6,579,318 B2 | 6/2003 | Varga et al. | |
| 6,579,319 B2 | 6/2003 | Goble et al. | |
| 6,589,244 B1 | 7/2003 | Sevrain et al. | |
| 6,600,956 B2 | 7/2003 | Maschino et al. | |
| 6,607,530 B1 | 8/2003 | Carl et al. | |
| 6,610,091 B1 | 8/2003 | Reiley | |
| D479,331 S | 9/2003 | Pike et al. | |
| 6,626,944 B1 | 9/2003 | Taylor | |
| 6,641,614 B1 | 11/2003 | Wagner et al. | |
| 6,656,178 B1 | 12/2003 | Veldhuizen et al. | |
| 6,656,195 B2 | 12/2003 | Peters et al. | |
| 6,669,697 B1 | 12/2003 | Pisharodi | |
| 6,669,729 B2 | 12/2003 | Chin | |
| 6,679,914 B1 | 1/2004 | Gabbay | |
| 6,706,068 B2 | 3/2004 | Ferree | |
| 6,743,232 B2 | 6/2004 | Overaker et al. | |
| 6,761,720 B1 | 7/2004 | Senegas | |
| 6,764,491 B2 | 7/2004 | Frey et al. | |
| 6,770,095 B2 | 8/2004 | Grinberg et al. | |
| 6,783,527 B2 | 8/2004 | Drewry et al. | |
| 6,790,210 B1 | 9/2004 | Cragg et al. | |
| 6,802,863 B2 | 10/2004 | Lawson et al. | |
| 6,811,567 B2 | 11/2004 | Reiley | |
| 6,902,566 B2 | 6/2005 | Zucherman et al. | |
| 6,908,484 B2 | 6/2005 | Zubok et al. | |
| 6,966,930 B2 | 11/2005 | Arnin et al. | |
| 6,974,478 B2 | 12/2005 | Reiley et al. | |
| 6,974,479 B2 | 12/2005 | Trieu | |
| 7,004,971 B2 | 2/2006 | Serhan et al. | |
| D517,404 S | 3/2006 | Schluter | |
| 7,008,429 B2 | 3/2006 | Golobek | |
| 7,013,675 B2 | 3/2006 | Marquez-Pickering | |
| 7,051,451 B2 | 5/2006 | Augostino et al. | |
| 7,074,238 B2 | 7/2006 | Stinson et al. | |
| 7,101,375 B2 | 9/2006 | Zucherman et al. | |
| 7,223,269 B2 | 5/2007 | Chappuis | |
| D565,180 S | 3/2008 | Schluter | |
| 7,371,238 B2 | 5/2008 | Sololeski et al. | |
| 7,458,981 B2 | 12/2008 | Fielding et al. | |
| 7,517,358 B2 | 4/2009 | Petersen | |
| 7,537,611 B2 | 5/2009 | Lee | |
| 7,559,940 B2 | 7/2009 | McGuire et al. | |
| 7,563,286 B2 | 7/2009 | Gerber et al. | |
| 7,585,300 B2 | 9/2009 | Cha | |
| 7,608,104 B2 | 10/2009 | Yuan et al. | |
| 7,695,472 B2 | 4/2010 | Young | |
| 7,799,077 B2 | 9/2010 | Lang et al. | |
| 7,806,895 B2 | 10/2010 | Weier et al. | |
| 7,846,183 B2 | 12/2010 | Blain | |
| 7,862,590 B2 | 1/2011 | Lim et al. | |
| 7,935,136 B2 | 5/2011 | Alamin et al. | |
| D643,121 S | 8/2011 | Milford et al. | |
| 7,993,370 B2 | 8/2011 | Jahng | |
| 7,998,172 B2 | 8/2011 | Blain | |
| 8,052,728 B2 | 11/2011 | Hestad | |
| 8,109,971 B2 | 2/2012 | Hale | |
| 8,133,225 B2 | 3/2012 | Pieske | |
| 8,163,016 B2 | 4/2012 | Linares | |
| 8,172,877 B2 | 5/2012 | Winslow et al. | |
| 8,177,810 B2 | 5/2012 | Ferree | |
| 8,192,468 B2 | 6/2012 | Biedermann et al. | |
| 8,216,275 B2 | 7/2012 | Fielding et al. | |
| 8,231,661 B2 | 7/2012 | Carls | |
| 8,246,655 B2 | 8/2012 | Jackson et al. | |
| 8,267,966 B2 | 9/2012 | McCormack et al. | |
| 8,292,954 B2 | 10/2012 | Robinson et al. | |
| 8,306,307 B2 | 11/2012 | Koike et al. | |
| 8,382,801 B2 | 2/2013 | Lamborne et al. | |
| 8,394,125 B2 | 3/2013 | Assell | |
| 8,460,346 B2 | 6/2013 | Ralph et al. | |
| 8,486,078 B2 | 7/2013 | Carl et al. | |
| 8,496,691 B2 | 7/2013 | Blain | |
| 8,579,903 B2 | 11/2013 | Carl | |
| 8,652,137 B2 | 2/2014 | Blain et al. | |
| 8,740,942 B2 | 6/2014 | Blain | |

(56) References Cited

U.S. PATENT DOCUMENTS

| | | |
|---|---|---|
| 8,740,949 B2 | 6/2014 | Blain |
| 8,753,345 B2 | 6/2014 | McCormack et al. |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| 9,101,410 B1 | 8/2015 | Urrea |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,439,686 B2 * | 9/2016 | Rooney ............... A61B 17/7089 |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| 9,615,861 B2 | 4/2017 | Perez-Cruet et al. |
| D790,062 S | 6/2017 | Blain et al. |
| 9,675,387 B2 | 6/2017 | Blain |
| 9,743,937 B2 | 8/2017 | Blain et al. |
| 9,808,294 B2 | 11/2017 | Blain |
| 9,820,784 B2 | 11/2017 | Blain et al. |
| 9,839,450 B2 | 12/2017 | Blain et al. |
| D810,942 S | 2/2018 | Blain et al. |
| D812,754 S | 3/2018 | Blain et al. |
| 9,936,984 B2 | 4/2018 | Blain |
| 10,022,161 B2 | 7/2018 | Blain |
| 10,085,776 B2 | 10/2018 | Blain |
| D834,194 S | 11/2018 | Blain et al. |
| 10,194,955 B2 | 2/2019 | Blain et al. |
| 10,251,679 B2 | 4/2019 | Blain et al. |
| D857,900 S | 8/2019 | Blain et al. |
| 10,368,921 B2 | 8/2019 | Blain |
| 10,426,524 B2 | 10/2019 | Blain |
| 10,624,680 B2 | 4/2020 | Blain |
| D884,896 S | 5/2020 | Blain et al. |
| 10,758,361 B2 | 9/2020 | Blain |
| D926,982 S | 8/2021 | Blain et al. |
| 11,272,961 B2 | 3/2022 | Blain et al. |
| 11,304,733 B2 | 4/2022 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0099444 A1 | 7/2002 | Boyd et al. |
| 2002/0120335 A1 | 8/2002 | Angelucci et al. |
| 2002/0123806 A1 | 9/2002 | Reiley |
| 2002/0138077 A1 | 9/2002 | Ferree |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0093152 A1 | 5/2003 | Pedersen et al. |
| 2003/0093154 A1 | 5/2003 | Estes et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0195727 A1 | 10/2004 | Stoy |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0107879 A1 | 5/2005 | Christensen et al. |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0154463 A1 | 7/2005 | Trieu |
| 2005/0159746 A1 | 7/2005 | Grab et al. |
| 2005/0171547 A1 | 8/2005 | Aram |
| 2005/0197700 A1 | 9/2005 | Boehem et al. |
| 2005/0204515 A1 | 9/2005 | Hewes |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 * | 1/2006 | Alamin ............... A61B 17/7064 606/74 |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149289 A1 | 7/2006 | Winslow et al. |
| 2006/0149375 A1 | 7/2006 | Yuan et al. |
| 2006/0190081 A1 | 8/2006 | Kraus et al. |
| 2006/0200137 A1 | 9/2006 | Soboleski et al. |
| 2006/0235412 A1 | 10/2006 | Blain |
| 2006/0241597 A1 | 10/2006 | Mitchell et al. |
| 2006/0241601 A1 | 10/2006 | Trautwein et al. |
| 2006/0241758 A1 | 10/2006 | Peterman et al. |
| 2006/0241778 A1 | 10/2006 | Ogilvie |
| 2006/0247650 A1 | 11/2006 | Yerby et al. |
| 2006/0293691 A1 | 12/2006 | Mitra et al. |
| 2007/0055236 A1 | 3/2007 | Hudgins et al. |

(56) References Cited

U.S. PATENT DOCUMENTS

| | | |
|---|---|---|
| 2007/0055252 A1 | 3/2007 | Blain et al. |
| 2007/0055373 A1 | 3/2007 | Hudgins et al. |
| 2007/0073293 A1* | 3/2007 | Martz ................ A61B 17/7062 606/86 A |
| 2007/0078464 A1 | 4/2007 | Jones et al. |
| 2007/0100452 A1 | 5/2007 | Prosser |
| 2007/0118218 A1 | 5/2007 | Hooper |
| 2007/0123863 A1 | 5/2007 | Winslow et al. |
| 2007/0135814 A1 | 6/2007 | Farris |
| 2007/0149976 A1 | 6/2007 | Hale et al. |
| 2007/0179619 A1 | 8/2007 | Grab |
| 2007/0250166 A1 | 10/2007 | McKay |
| 2007/0255414 A1 | 11/2007 | Melkent et al. |
| 2007/0270812 A1 | 11/2007 | Peckham |
| 2008/0009866 A1 | 1/2008 | Alamin et al. |
| 2008/0046083 A1 | 2/2008 | Hewko |
| 2008/0058929 A1 | 3/2008 | Whelan |
| 2008/0082103 A1 | 4/2008 | Hutton et al. |
| 2008/0082172 A1 | 4/2008 | Jackson |
| 2008/0161853 A1 | 7/2008 | Arnold et al. |
| 2008/0177264 A1 | 7/2008 | Alamin et al. |
| 2008/0177326 A1 | 7/2008 | Thompson |
| 2008/0183209 A1 | 7/2008 | Robinson et al. |
| 2008/0183211 A1 | 7/2008 | Lamborne et al. |
| 2008/0228225 A1 | 9/2008 | Trautwein et al. |
| 2008/0255664 A1 | 10/2008 | Hogendijk et al. |
| 2008/0262549 A1 | 10/2008 | Bennett et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0036926 A1 | 2/2009 | Hestad |
| 2009/0072006 A1 | 3/2009 | Clauson et al. |
| 2009/0076617 A1 | 3/2009 | Ralph et al. |
| 2009/0105766 A1 | 4/2009 | Thompson et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0198339 A1 | 8/2009 | Kleiner et al. |
| 2009/0248077 A1 | 10/2009 | Johns |
| 2009/0248082 A1 | 10/2009 | Crook et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0306716 A1 | 12/2009 | Beger et al. |
| 2009/0326589 A1 | 12/2009 | Lemoine et al. |
| 2010/0004657 A1 | 1/2010 | Dudasik |
| 2010/0010548 A1 | 1/2010 | Hermida Ochoa |
| 2010/0063550 A1 | 3/2010 | Felix et al. |
| 2010/0076503 A1 | 3/2010 | Beyar et al. |
| 2010/0087859 A1 | 4/2010 | Jackson, Jr. |
| 2010/0131008 A1 | 5/2010 | Overes et al. |
| 2010/0168864 A1 | 7/2010 | White et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0256680 A1 | 10/2010 | Pasquet et al. |
| 2010/0274289 A1 | 10/2010 | Carls et al. |
| 2010/0292698 A1* | 11/2010 | Hulliger ................ A61B 17/80 606/74 |
| 2010/0298829 A1 | 11/2010 | Schaller et al. |
| 2010/0318133 A1 | 12/2010 | Tornier |
| 2011/0015744 A1 | 1/2011 | Squires et al. |
| 2011/0022050 A1 | 1/2011 | McClellan et al. |
| 2011/0034956 A1 | 2/2011 | Mazda et al. |
| 2011/0060366 A1 | 3/2011 | Heim et al. |
| 2011/0082504 A1 | 4/2011 | Singhatat et al. |
| 2011/0098816 A1 | 4/2011 | Jacob et al. |
| 2011/0106163 A1 | 5/2011 | Hochschuler et al. |
| 2011/0106259 A1 | 5/2011 | Lindenmann et al. |
| 2011/0160772 A1 | 6/2011 | Arcenio et al. |
| 2011/0172712 A1 | 7/2011 | Chee et al. |
| 2011/0245875 A1 | 10/2011 | Karim |
| 2011/0295318 A1 | 12/2011 | Alamin et al. |
| 2011/0301644 A1 | 12/2011 | Belliard |
| 2012/0022591 A1 | 1/2012 | Baccelli et al. |
| 2012/0022649 A1 | 1/2012 | Robinson et al. |
| 2012/0035658 A1 | 2/2012 | Goble et al. |
| 2012/0041441 A1 | 2/2012 | Bernstein et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0197643 A1 | 8/2013 | Greenberg et al. |
| 2013/0204250 A1 | 8/2013 | McDevitt et al. |
| 2013/0253649 A1 | 9/2013 | Davis |
| 2013/0261625 A1 | 10/2013 | Koch et al. |
| 2013/0325065 A1 | 12/2013 | Malandain et al. |
| 2014/0012318 A1 | 1/2014 | Goel |
| 2014/0018816 A1 | 1/2014 | Fenn et al. |
| 2014/0066758 A1 | 3/2014 | Marik et al. |
| 2014/0214084 A1 | 7/2014 | Jackson et al. |
| 2014/0257397 A1 | 9/2014 | Akbarnia et al. |
| 2014/0277149 A1 | 9/2014 | Rooney et al. |
| 2014/0309699 A1 | 10/2014 | Houff |
| 2014/0336653 A1 | 11/2014 | Bromer |
| 2014/0378976 A1 | 12/2014 | Garcia |
| 2015/0045794 A1 | 2/2015 | Garcia et al. |
| 2015/0119988 A1 | 4/2015 | Assell et al. |
| 2015/0164652 A1 | 6/2015 | Assell et al. |
| 2015/0190149 A1 | 7/2015 | Assell et al. |
| 2015/0209096 A1 | 7/2015 | Gephart |
| 2015/0313656 A1* | 11/2015 | Hulliger ................ A61B 17/82 606/74 |
| 2015/0327872 A1 | 11/2015 | Assell et al. |
| 2015/0342648 A1 | 12/2015 | McCormack et al. |
| 2015/0342657 A1* | 12/2015 | Voisard ............... A61B 17/8863 606/103 |
| 2016/0113692 A1 | 4/2016 | Knoepfle |
| 2016/0128838 A1 | 5/2016 | Assell et al. |
| 2016/0213481 A1 | 7/2016 | Blain |
| 2017/0239060 A1 | 8/2017 | Blain |
| 2017/0281232 A1 | 10/2017 | Smith |
| 2017/0296234 A1 | 10/2017 | Jackson et al. |
| 2017/0333091 A1 | 11/2017 | Taber et al. |
| 2017/0333205 A1 | 11/2017 | Joly et al. |
| 2018/0132915 A1* | 5/2018 | Esser ................... A61B 17/823 |
| 2019/0142478 A1 | 5/2019 | Blain |
| 2019/0167314 A1 | 6/2019 | Mosnier et al. |
| 2019/0192194 A1 | 6/2019 | Blain |
| 2019/0328428 A1 | 10/2019 | Blain |
| 2019/0365433 A1 | 12/2019 | Blain et al. |
| 2020/0000608 A1 | 1/2020 | Bullard |
| 2020/0214746 A1 | 7/2020 | Blain et al. |
| 2021/0000608 A1 | 1/2021 | Blain et al. |
| 2021/0121207 A1 | 4/2021 | Semingson |
| 2021/0251667 A1* | 8/2021 | Blain ................ A61B 17/7053 |
| 2022/0151659 A1 | 5/2022 | Smith et al. |
| 2022/0175424 A1 | 6/2022 | Blain et al. |
| 2022/0218394 A1 | 7/2022 | Blain et al. |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |

(56) References Cited

FOREIGN PATENT DOCUMENTS

| | | |
|---|---|---|
| EP | 1 201 256 | 5/2002 |
| EP | 2 138 122 | 12/2009 |
| EP | 2 919 717 | 9/2015 |
| FR | 2 704 745 | 11/1994 |
| FR | 2 722 980 | 2/1996 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 08-509918 | 10/1996 |
| JP | 10-179622 | 7/1998 |
| JP | 2000-201941 | 7/2000 |
| JP | 2000-210297 | 8/2000 |
| JP | 2003-079649 | 3/2003 |
| JP | 2004-508888 | 3/2004 |
| JP | 2004-181236 | 7/2004 |
| JP | 2004-537354 | 12/2004 |
| JP | 2006-230722 | 9/2006 |
| JP | 2006-528540 | 12/2006 |
| JP | 2007-503884 | 3/2007 |
| JP | 2007-517627 | 7/2007 |
| JP | 2007-190389 | 8/2007 |
| JP | 2008-510526 | 4/2008 |
| JP | 2008-522787 | 7/2008 |
| JP | 2008-537498 | 9/2008 |
| JP | 2009-533167 | 9/2009 |
| JP | 2010-510852 | 4/2010 |
| JP | 2010-173739 | 8/2010 |
| JP | 2012-509740 | 4/2012 |
| JP | 2012-521221 | 9/2012 |
| JP | 2013-534451 | 9/2013 |
| JP | 2013-535247 | 9/2013 |
| JP | 2014-513583 | 6/2014 |
| JP | 2014-523751 | 9/2014 |
| JP | 2015-500701 | 1/2015 |
| MX | 6012309 | 1/2007 |
| WO | WO 88/006022 | 8/1988 |
| WO | WO 93/014721 | 8/1993 |
| WO | WO 94/004088 | 3/1994 |
| WO | WO 97/047246 | 12/1997 |
| WO | WO 98/048717 | 11/1998 |
| WO | WO 99/023963 | 5/1999 |
| WO | WO 00/038582 | 7/2000 |
| WO | WO 00/053126 | 9/2000 |
| WO | WO 01/030248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2008/008522 | 1/2008 |
| WO | WO 2009/013397 | 1/2009 |
| WO | WO 2009/015100 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2012/116267 | 8/2012 |
| WO | WO 2012/154265 | 11/2012 |
| WO | WO 2013/022880 | 2/2013 |
| WO | WO 2013/138655 | 9/2013 |
| WO | WO 2014/078541 | 5/2014 |
| WO | WO 2020/030656 | 2/2020 |
| WO | WO 2020/236229 | 11/2020 |

OTHER PUBLICATIONS

Official Communication in Australian Application No. 2019201539, dated Apr. 3, 2020.
3rd Party Lab Notebook, "Facet Cartilage Repair," dated May 20, 2003 in 2 pages.
ArthroTek, "CurvTek® Bone Tunneling System," Surgical Technique, 2000, pp. 6.
ArthroTek, "CurvTek® Bone Tunneling System," User's Manual, 2000, pp. 20.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", Spine, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
E-mail from 3rd Party citing U.S. Appl. Nos. 60/749,000; 60/749,000 and 60/749,000, initial e-mail dated May 11, 2009, reply e-mail dated May 18, 2009.
Frost, Harold M., "From Wolff's Law to the Utah Paradigm: Insights About Bone Physiology and Its Clinical Applications", The Anatomical Record, 2001, vol. 262, pp. 398-419.
King et al., "Mechanism of Spinal Injury Due to Caudocephalad Acceleration," Symposium on the Lumbar Spine, Orthopedic Clinic of North America, Jan. 1975, vol. 6, pp. 19-31.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", Spine, 1993, vol. 18, No. 10, pp. 1298-1310.
PARTEQ Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (Injury), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Sharpe Products, "Metal Round Disks", https://web.archive.org/web/20170705214756/https://sharpeproducts.com/store/metal-round-disks, as archived Jul. 5, 2017 in 3 pages.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.

(56) References Cited

OTHER PUBLICATIONS

Official Communication in Australian Application No. 2013237744, dated Sep. 2, 2014.
Notice of Acceptance in Australian Application No. 2013237744, dated Apr. 23, 2015.
Official Communication in Australian Application No. 2015205875, dated Apr. 2, 2016.
Official Communication in Australian Application No. 2015205875, dated Jun. 15, 2016.
Official Communication in Australian Application No. 2016231622, dated Dec. 5, 2017.
Official Communication in Australian Application No. 2016231622, dated Nov. 22, 2018.
Notice of Acceptance in Australian Application No. 2016231622, dated Dec. 4, 2018.
Official Communication in Australian Application No. 2019201539, dated Jun. 25, 2019.
Official Communication in Canadian Application No. 2,555,355, dated Sep. 2, 2011.
Official Communication in Canadian Application No. 2,803,783, dated Sep. 29, 2014.
Official Communication in Canadian Application No. 2,803,783, dated Aug. 5, 2015.
Official Communication in Canadian Application No. 2,803,783, dated Jul. 7, 2016.
Official Communication in Canadian Application No. 2,803,783, dated Apr. 5, 2017.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in European Application No. 16180368.9, dated Mar. 31, 2017.
Official Communication in European Application No. 16180368.9, dated Jan. 11, 2018.
Official Communication in European Application No. 19158915.9, dated Jul. 1, 2019.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report on Patentability and Written Opinion in International Application No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability and Written Opinion in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in Canadian Application No. 2,804,223, dated Jun. 5, 2017.
Official Communication in Canadian Application No. 2,804,223, dated Mar. 14, 2018.
Official Communication in European Application No. 11818586.7, dated Nov. 6, 2014.
Official Communication in European Application No. 11818586.7, dated Feb. 3, 2017.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
Official Communication in Japanese Application No. 2015-242990, dated May 8, 2017.
Official Communication in Japanese Application No. 2015-242990, dated Aug. 21, 2017.
International Search Report and Written Opinion in International Application No. PCT/US2011/047432, dated Dec. 12, 2011.
International Preliminary Report on Patentability and Written Opinion in International Application No. PCT/US2011/047432, dated Feb. 28, 2013.
Official Communication in Australian Application No. 2012222229, dated Aug. 21, 2015.
Official Communication in Australian Application No. 2012222229, dated May 11, 2016.
Official Communication in Australian Application No. 2012222230, dated Aug. 21, 2015.
Official Communication in European Application No. EP12749447.4, dated Jan. 4, 2017.
Official Communication in European Application No. EP12749447.4, dated Apr. 4, 2017.
Official Communication in European Application No. EP12749447.4, dated Nov. 14, 2018.
Official Communication in European Application No. 12749251.0, dated Jan. 4, 2017.
Official Communication in European Application No. 12749251.0, dated May 9, 2017.
Official Communication in European Application No. 12749251.0, dated Aug. 16, 2019.
Official Communication in Japanese Application No. 2013-555591, dated Jan. 4, 2016.
Official Communication in Japanese Application No. 2013-555591, dated Nov. 21, 2016.
Official Communication in Japanese Application No. 2016-246368, dated Oct. 30, 2017.
Official Communication in Japanese Application No. 2016-246368, dated Jul. 2, 2018.
Official Communication in Japanese Application No. 2013-555592, dated Dec. 7, 2015.
Official Communication in Japanese Application No. 2013-555592, dated Aug. 8, 2016.
Official Communication in Japanese Application No. 2013-555592, dated Jan. 5, 2018.
Official Communication in Japanese Application No. 2016-237460, dated Oct. 23, 2017.

(56) References Cited

OTHER PUBLICATIONS

Official Communication in Japanese Application No. 2016-237460, dated Apr. 16, 2018.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in Australian Application No. 2014241989, dated Aug. 31, 2017.
Official Communication in Australian Application No. 2014241989, dated Jun. 20, 2018.
Official Communication in Australian Application No. 2014241989, dated Aug. 17, 2018.
Official Communication in Australian Application No. 2018279003, dated Jan. 9, 2020.
Official Communication in Canadian Application No. 2,903,999, dated Dec. 9, 2019.
Official Communication in European Application No. 14774714.1, dated Oct. 21, 2016.
Official Communication in European Application No. 14774714.1, dated May 23, 2019.
Official Communication in Japanese Application No. 2016-500490, dated Nov. 27, 2017.
Official Communication in Japanese Application No. 2016-500490, dated May 7, 2018.
International Search Report and Written Opinion in International Application No. PCT/US2014/019302, dated May 18, 2015.
Official Communication in Australian Application No. 2014241994, dated Oct. 30, 2017.
Official Communication in Australian Application No. 2014241994, dated Jan. 31, 2020.
Official Communication in Canadian Application No. 2,904,280, dated Dec. 9, 2019.
Official Communication in European Application No. 14776445.0, dated Nov. 7, 2016.
Official Communication in Japanese Application No. 2016-500498, dated Jan. 5, 2018.
Official Communication in Japanese Application No. 2016-500498, dated Jul. 2, 2018.
Official Communication in Japanese Application No. 2016-500498, dated Mar. 4, 2019.
Official Communication in Japanese Application No. 2016-500498, dated Aug. 9, 2019.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in Australian Application No. 2014327083, dated May 31, 2018.
Notice of Acceptance in Australian Application No. 2014327083, dated Apr. 3, 2019.
Official Communication in European Application No. 14850082.0, dated Aug. 31, 2016.
Official Communication in Japanese Application No. 2016-517392, dated Jun. 4, 2018.
Official Communication in Japanese Application No. 2016-517392, dated Apr. 22, 2019.
Official Communication in Japanese Application No. 2016-517392, dated Dec. 2, 2019.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
Official Communication in Australian Application No. 2016212009, dated Sep. 6, 2019.
Official Communication in European Application No. 16743832.4, dated Jul. 24, 2018.
Official Communication in Japanese Application No. 2017-557269, dated Oct. 21, 2019.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
Official Communication in Australian Application No. 2020244544, dated Nov. 15, 2021.
Official Communication in European Application No. 11818586.7, dated Apr. 8, 2021.
Official Communication in European Application No. EP12749447.4, dated Aug. 18, 2021.
Official Communication in Australian Application No. 2018279003, dated Sep. 18, 2020.
Official Communication in Australian Application No. 2018279003, dated Jan. 12, 2021.
Official Communication in Canadian Application No. 2,903,999, dated Aug. 31, 2020.
Official Communication in Canadian Application No. 2,904,280, dated Sep. 1, 2020.
Official Communication in Canadian Application No. 2,904,280, dated Jun. 7, 2021.
Official Communication in European Application No. 14776445.0, dated Jun. 10, 2021.
Official Communication in Japanese Application No. 2019-163133, dated Oct. 5, 2020.
Official Communication in Japanese Application No. 2019-163133, dated Jun. 7, 2021.
Official Communication in Australian Application No. 2019206045, dated Sep. 8, 2020.
Official Communication in Australian Application No. 2019206045, dated Sep. 9, 2020.
Official Communication in Australian Application No. 2019206045, dated Jul. 16, 2021.
Official Communication in Canadian Application No. 2,923,623, dated Dec. 8, 2020.
Official Communication in European Application No. 14850082.0, dated Sep. 15, 2020.
Official Communication in Japanese Application No. 2019-236855, dated Nov. 24, 2020.
Official Communication in Japanese Application No. 2019-236855, dated Jun. 28, 2021.
Official Communication in Australian Application No. 2016212009, dated May 26, 2020.
Official Communication in Australian Application No. 2016212009, dated Jul. 14, 2020.
Official Communication in Austra2020281016lian Application No. 2016212009, dated Nov. 24, 2021.
Official Communication in Canadian Application No. 2,972,788, dated Jan. 31, 2022.
Official Communication in Japanese Application No. 2017-557269, dated Jul. 13, 2020.
Official Communication in Japanese Application No. 2017-557269, dated Nov. 1, 2021.
Official Communication in Japanese Application No. 2020-181320, Sep. 21, 2021.
International Preliminary Report on Patentability and Written Opinion in International Application No. PCT/US2020/014985, dated Dec. 2, 2021.

(56) References Cited

OTHER PUBLICATIONS

Invitation to Pay Additional Search Fees in International Application No. PCT/US2021/072351, dated Jan. 13, 2022.
International Search Report and Written Opinion in International Application No. PCT/US2021/017643, dated Apr. 28, 2021.
International Search Report and Written Opinion in International Application No. PCT/US2021/072351, dated Mar. 18, 2022.
Official Communication in Australian Application No. 2020244544, dated Apr. 27, 2022.
Official Communication in Australian Application No. 2020244544, dated Jun. 8, 2022.
Official Communication in Australian Application No. 2021202409, dated Jul. 9, 2022.
Official Communication in Australian Application No. 2021203165, dated Jun. 8, 2022.
Official Communication in Canadian Application No. 2,904,280, dated Apr. 1, 2022.
Official Communication in European Application No. 14776445.0, dated May 20, 2022.
International Search Report and Written Opinion in International Application No. PCT/US2022/070851, dated May 13, 2022.

\* cited by examiner

BONE TIE AND BONE TIE INSERTER

CROSS-REFERENCE TO RELATED APPLICATIONS

This application claims priority benefit to U.S. Provisional Patent Application No. 62/851,410, filed May 22, 2019, the entirety of which is hereby incorporated by reference herein.

BACKGROUND

Field

Some embodiments described herein relate generally to systems and methods for performing spinal fusion and, in particular, to bone ties and bone tie inserters.

DESCRIPTION OF THE RELATED ART

Traumatic, inflammatory, and degenerative disorders of the spine can lead to severe pain and loss of mobility. According to some studies, back and spinal musculoskeletal impairments are the leading causes of lost work productivity in the United States. Pain as a result of some type of spinal impairment may have its source in a variety of pathologies or clinical conditions.

One source for back and spine pain is related to degeneration of the facets of the spine or facet arthritis. Bony contact or grinding of degenerated facet joint surfaces may play a role in some pain syndromes. While many technological advances have focused on the spinal disc and artificial replacement or repair of the disc, little advancement in facet repair has been made. Facet joint and disc degeneration frequently occur together. Thus, there is a need to address the clinical concerns raised by degenerative facet joints.

The current standard of care to address the degenerative problems with the facet joints is to fuse the two adjacent vertebrae together. By performing this surgical procedure, the relative motion between the two adjacent vertebrae is stopped, thus stopping motion of the facets and any potential pain generated as a result thereof. This surgical procedure has a high rate of morbidity and can potentially lead to further clinical complications such as adjacent segment disorders. This procedure is also not reversible. Therefore, if the patient has an unsatisfactory result, they may be subject to additional surgical fusion procedures.

SUMMARY

Devices and methods are disclosed for treating the vertebral column. In some embodiments, a bone tie for securing or fusing facets is provided. In some embodiments, a bone tie inserter is provided. In some embodiments, a method of use to treat the spine is provided.

In some embodiments, a bone tie for treating the spine is provided. The bone tie can include a proximal end and a distal end. The bone tie can include a head section comprising a rounded head. The bone tie can include a neck section extending proximally from the head section.

In some embodiments, the bone tie can include a body section extending proximally from the neck section, wherein the body section comprises one or more gears. In some embodiments, the bone tie can include a fastener section, wherein the fastener section comprises a ratchet. In some embodiments, the bone tie can include a body section extending proximally from the neck section, wherein the body section comprises a groove. In some embodiments, the head section comprises a flange. In some embodiments, the head section comprises a radiopaque marker.

In some embodiments, a bone tie inserter for placing a bone tie for treating the spine is provided. The bone tie inserter can include a bone tie advancer. The bone tie advancer can include a shaft. The bone tie advancer can include an advancer portion comprising a curved surface configured to guide a rounded head of a bone tie. The bone tie inserter can include a bone tie retriever. The bone tie retriever can include a shaft. The bone tie retriever can include a retriever portion configured to receive the rounded head. In some embodiments, the rounded head of the bone tie is configured to pivot and/or rotate within the retriever portion.

In some embodiments, the bone tie inserter can include the bone tie. In some embodiments, the advancer portion comprises a curve. In some embodiments, the retriever portion comprises a ledge. In some embodiments, the retriever portion comprises a channel. In some embodiments, the retriever portion is configured to receive the rounded head of a bone tie. In some embodiments, the advancer portion comprises a channel configured to receive a neck section extending proximally from the rounded head.

In some embodiments, a method of treating bone portions is provided. The method can include forming a lumen in a first bone portion. The method can include forming a lumen in a second bone portion. The method can include advancing a rounded head of a bone tie with a bone tie advancer through the lumen of the first bone portion and into the lumen of the second bone portion. In some embodiments, the bone tie advancer is removably coupled to the rounded head or a neck section extending from the rounded head. The method can include advancing the rounded head of the bone tie into a retriever portion of a bone tie retriever. In some embodiments, the retriever portion comprises a channel to receive the rounded head. The method can include withdrawing the bone tie retriever from the second bone portion, wherein the bone tie is configured to pivot and/or rotate as the bone tie retriever is withdrawn.

In some embodiments, the bone tie advancer comprises a channel to receive the neck section of the bone tie. In some embodiments, the bone tie advancer comprises a curve. In some embodiments, the bone tie advancer comprises a rounded section to abut the rounded head of the bone tie. In some embodiments, the bone tie retriever comprises an opening, wherein the neck section pivots, or pivots and rotates, from extending from the channel to extending through the opening. In some embodiments, the bone tie retriever comprises one or more retention features configured to retain the bone tie. In some embodiments, the bone tie retriever comprises a ledge. In some embodiments, the ledge facilitates pivoting and/or rotating of the rounded head of the bone tie.

BRIEF DESCRIPTION OF THE DRAWINGS

The structure and method of use will be better understood with the following detailed description of embodiments, along with the accompanying illustrations, in which.

DETAILED DESCRIPTION

Figure 1:
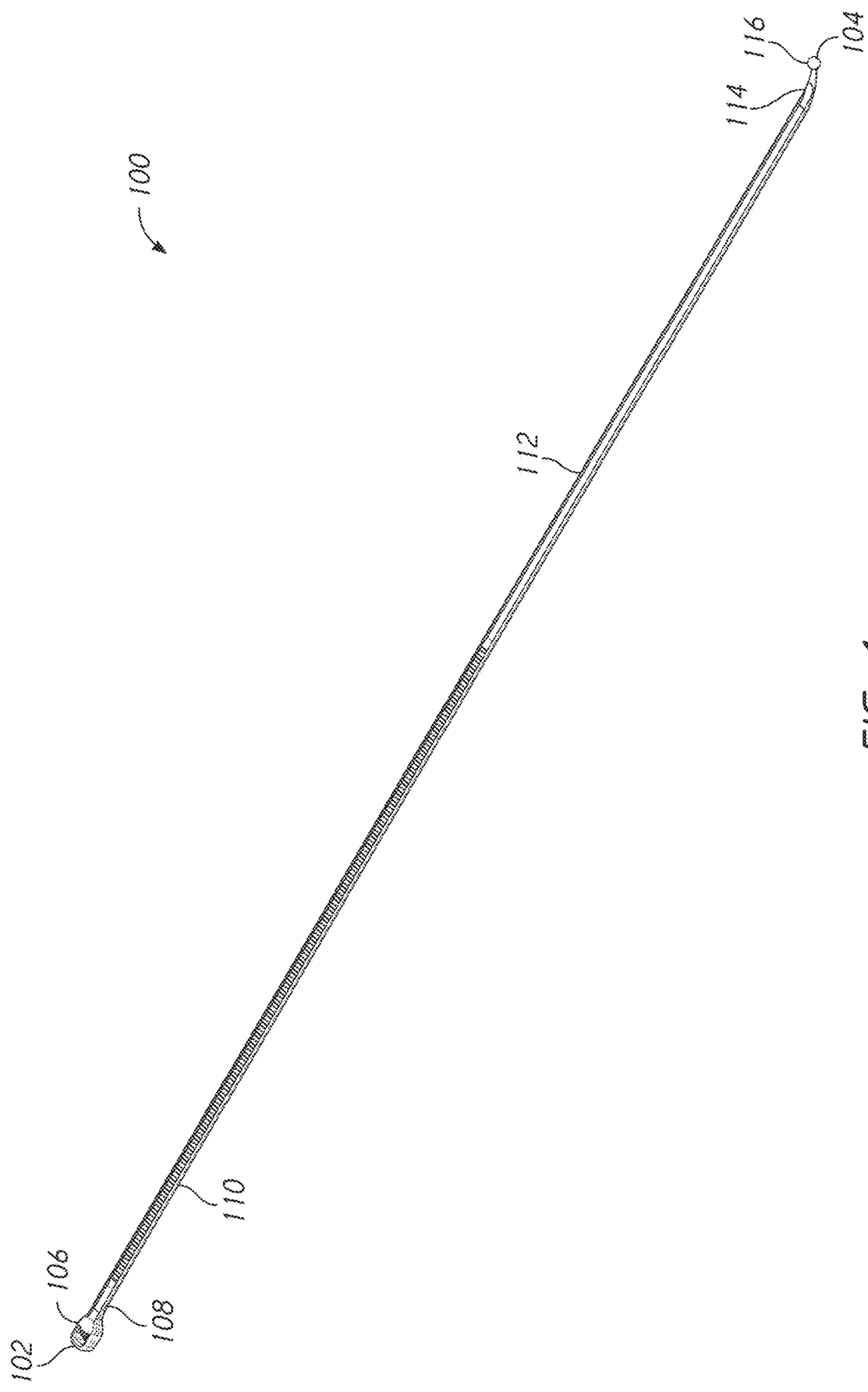
FIG. 1 is a perspective front view of an embodiment of a bone tie.

Although certain preferred embodiments and examples are disclosed below, it will be understood by those in the art that the disclosure extends beyond the specifically disclosed embodiments and/or uses of the invention and obvious modifications and equivalents thereof. Thus, it is intended that the scope should not be limited by the particular disclosed embodiments described below.

The systems and methods described herein relate to embodiments of bone ties, embodiments of bone ties inserters, and methods of use. The bone tie inserter can facilitate insertion of bone tie, as described herein. The bone tie can be inserted within a bone lumen, such as a bone lumen between adjacent vertebrae. The bone tie can be advanced by a bone tie advancer. The bone tie can be received by a bone tie retriever. In some embodiments, the bone tie pivots and/or rotates as the bone tie is withdrawn from the bone lumen between adjacent vertebrae.

1. Anatomy of the Spine

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-L5), five fused sacral (S1-S5) and four fused coccygeal vertebrae. Each typical thoracic vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae. The facet joints are true synovial joints with cartilaginous surfaces and a joint capsule.

The orientation of the facet joints vary, depending on the level of the vertebral column. In the C1 and C2 vertebrae, the facet joints are parallel to the transverse plane. In the C3 to C7 vertebrae, the facets are oriented at a 45 degree angle to the transverse plane and parallel to the frontal plane, respectively. This orientation allows the facet joints of the cervical vertebrae to flex, extend, lateral flex and rotate. At a 45 degree angle in the transverse plane, the facet joints of the cervical spine can guide, but do not limit, the movement of the cervical vertebrae. For the thoracic vertebrae, the facets are oriented at a 60 degree angle to the transverse plane and a 20 degree angle to the frontal plane, respectively. This orientation is capable of providing lateral flexion and rotation, but only limited flexion and extension. For the lumbar region, the facet joints are oriented at 90 degree angles to the transverse plane and a 45 degree angle to the frontal plane, respectively. The lumbar vertebrae are capable of flexion, extension and lateral flexion, but little, if any, rotation because of the 90 degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

2. Bone Tie

Figure 2:
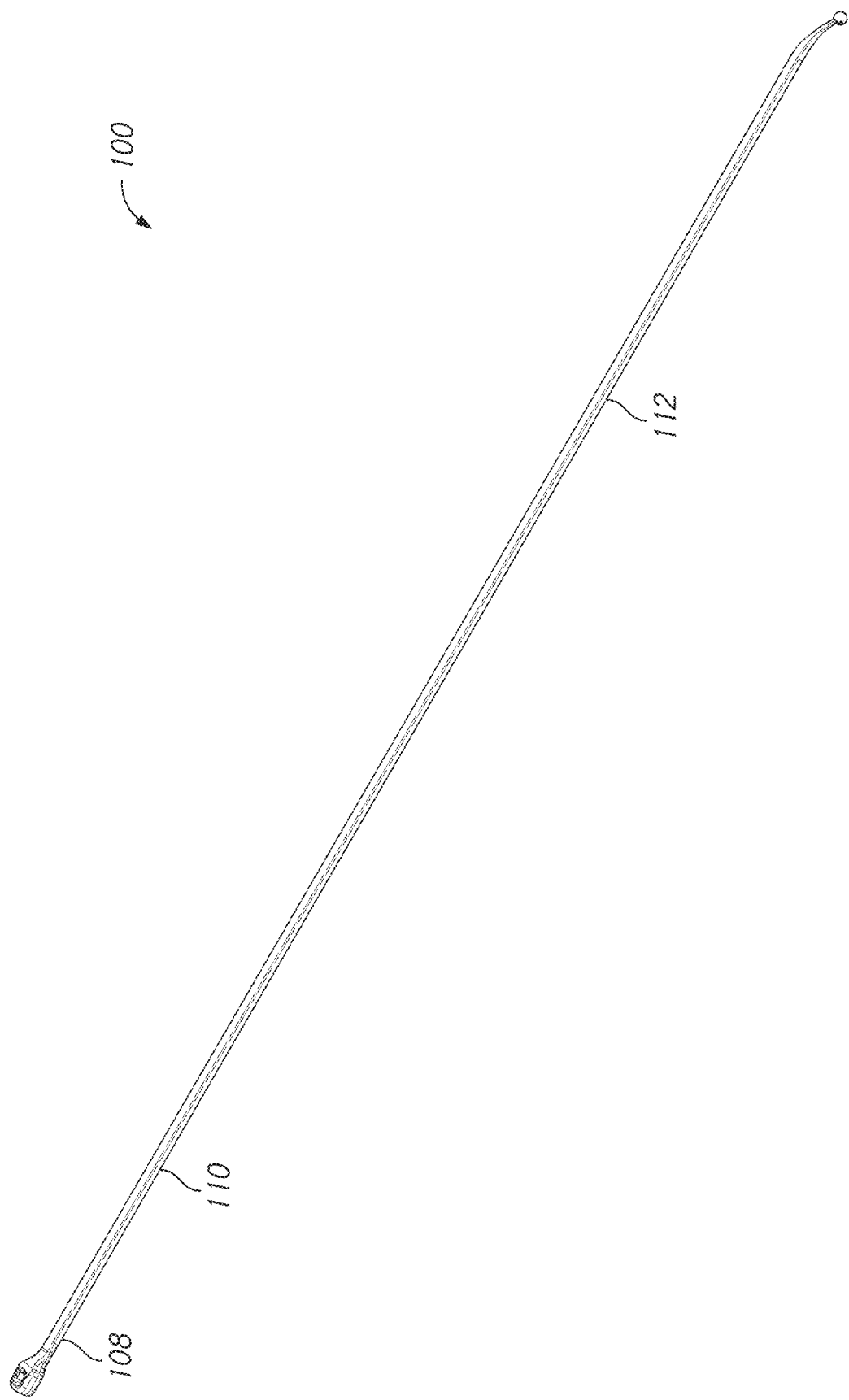
FIG. 2 is a perspective back view of the bone tie of FIG. 1.
Figure 3:
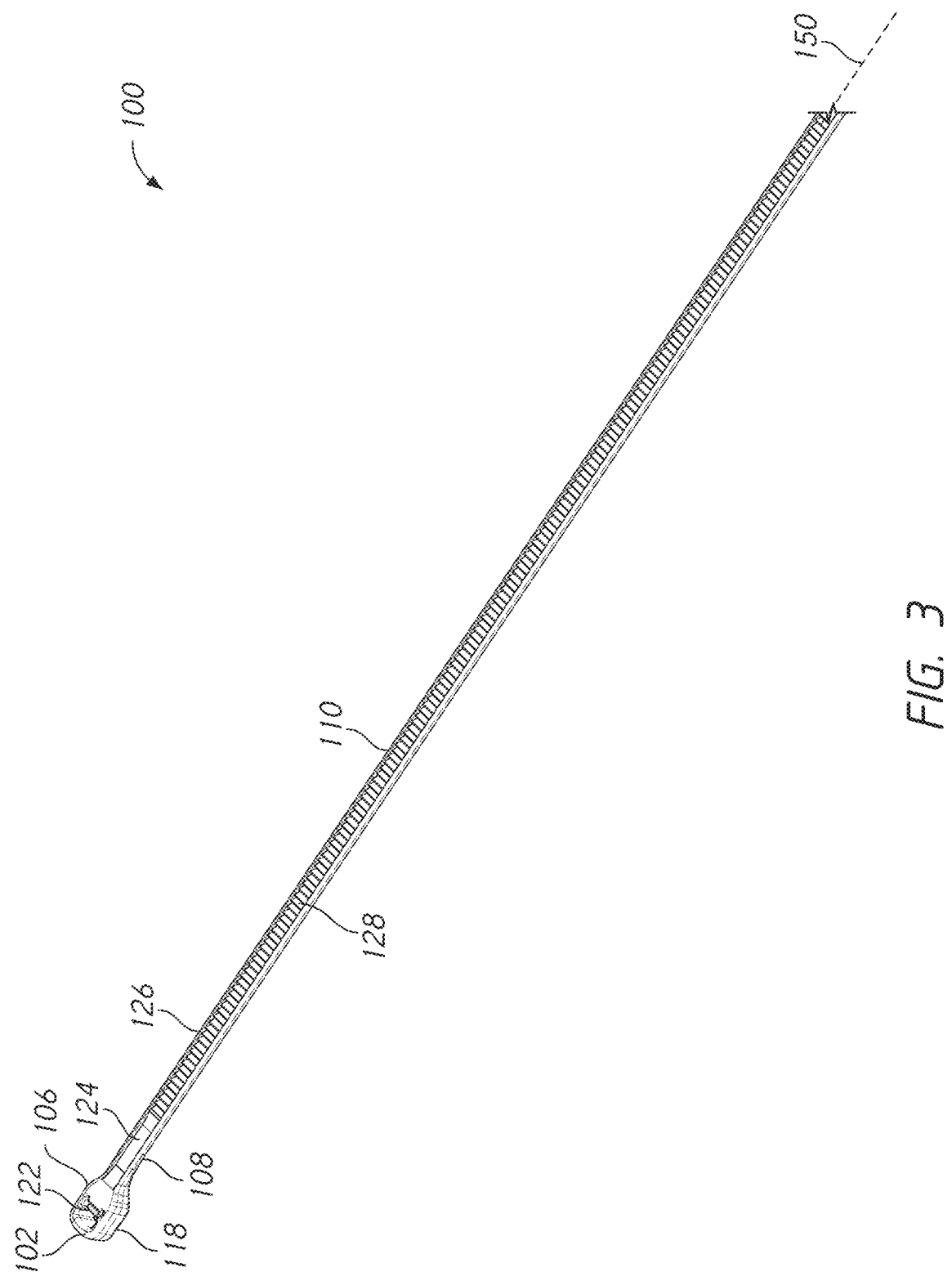
FIG. 3 is a perspective view of a proximal portion of the bone tie of FIG. 1.
Figure 4:
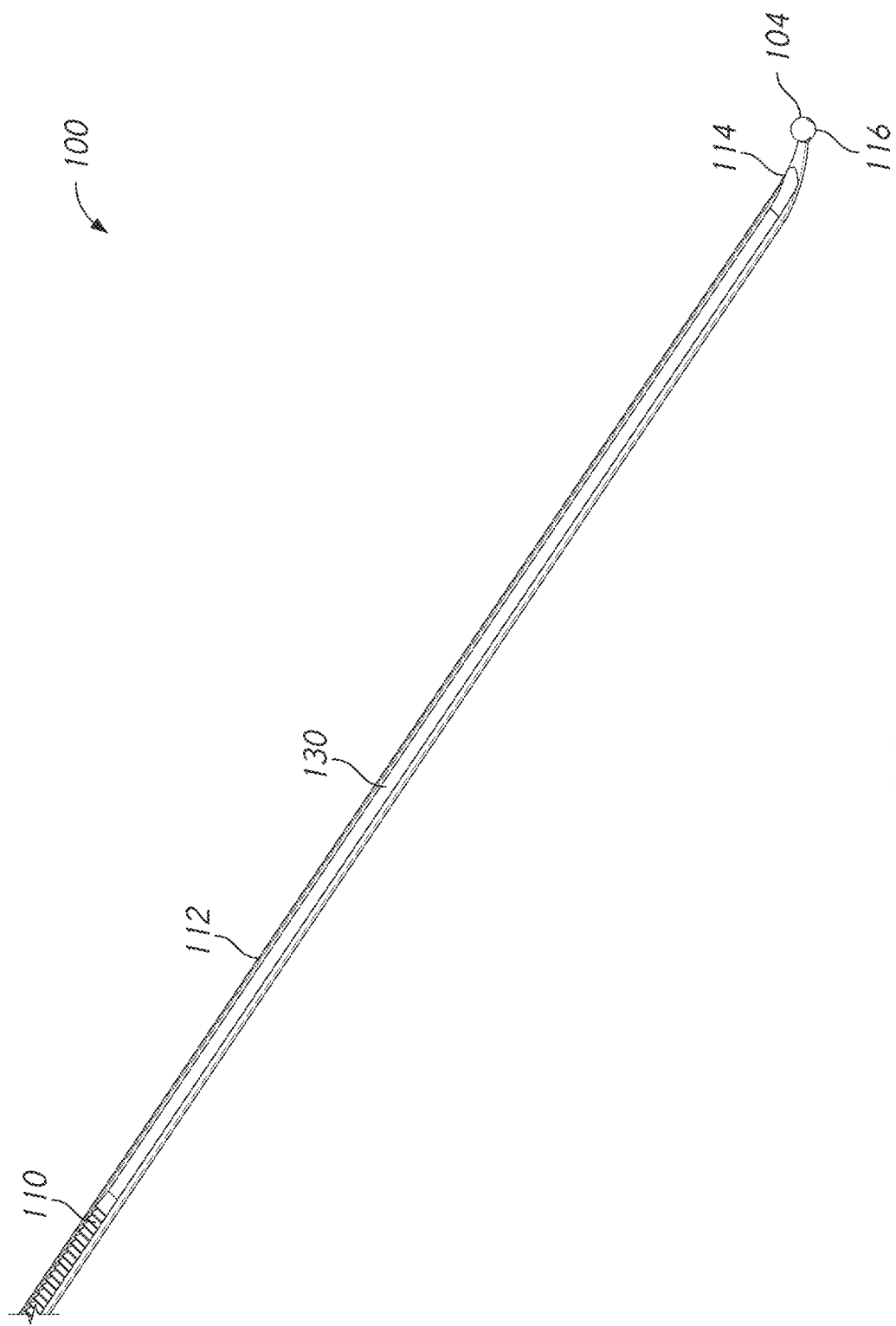
FIG. 4 is a perspective view of a distal portion of the bone tie of FIG. 1.
Figure 5:
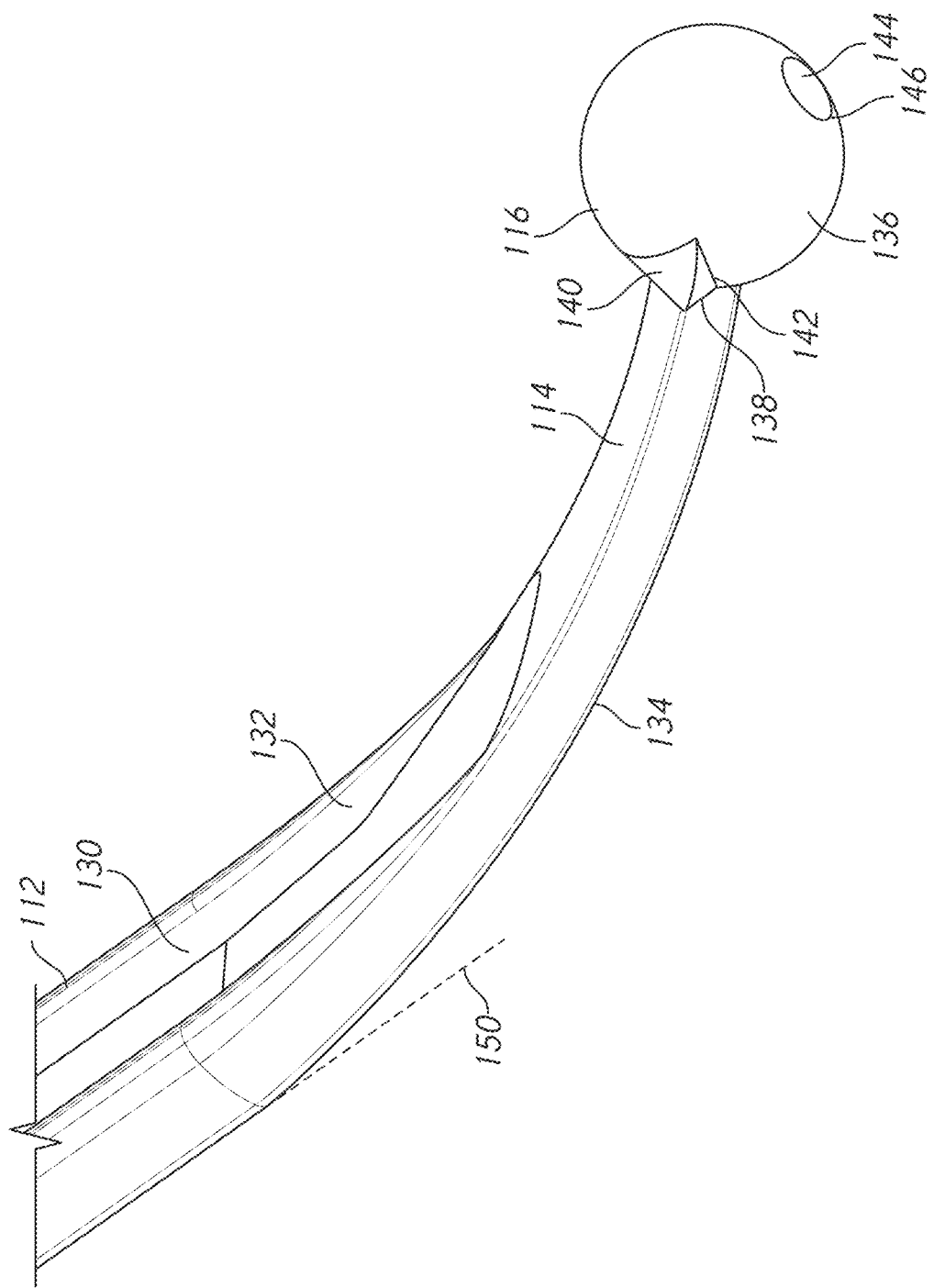
FIG. 5 is an enlarged perspective view of a distal portion of the bone tie of FIG. 1.

FIGS. 1-5 depict views of an embodiment of a bone tie 100. FIG. 1 illustrates a perspective front view. FIG. 2 illustrates a perspective back view. FIG. 3 illustrates a perspective view of a proximal portion of the bone tie 100. FIG. 4 illustrates a perspective view of a distal portion of the bone tie 100. FIG. 5 illustrates an enlarged perspective view of a distal portion of the bone tie 100.

The bone tie 100 can be a generally elongate member. The bone tie 100 can comprise a proximal end 102 and a distal end 104. The bone tie 100 can include a length between the proximal end 102 and the distal end 104. The proximal end 102 can be configured to be near the hands of the user when the user is manipulating the bone tie inserter as described herein. The distal end 104 can be configured to be inserted into a bone lumen as described herein. The distal end 104 can be configured to be the first portion of the bone tie 100 that is inserted in the lumen. The distal end 104 can be the leading end of the bone tie 100. In some methods of use, the proximal end 102 extends away from the vertebrae during insertion of the bone tie 100. In some methods of use, the proximal end 102 is held by the user. In some methods of use, the proximal end 102 is unconstrained during insertion of the bone tie 100. In some methods of use, only a portion of the bone tie 100 near the distal end 104 is grasped and manipulated by the bone tie inserter as described herein. In some methods of use, a portion of the bone tie 100 near the proximal end 102 is retained along the bone tie inserter.

The bone tie 100 can include one or more sections along the length of the bone tie 100. The sections can have a different shape, configuration, or function than an adjacent section of the bone tie 100. In some embodiments, one or more non-adjacent sections can have the same shape, configuration, or function as another section of the bone tie 100. In some embodiments, one or more additional sections are provided. In some embodiments, one or more of the sections provided herein are omitted.

The bone tie 100 can include a fastener section 106. The fastener section 106 can be located at or near the proximal end 102. The fastener section 106 can include any mechanism configured to secure the fastener section 106 to another section of the bone tie 100. The fastener section 106 can include a mechanism that allows the bone tie 100 to be secured in a single direction of travel such as a ratchet. The fastener section 106 can include a mechanism that allows the bone tie 100 to be secured in two directions of travel such as a pair of gears.

The bone tie 100 can include a first section 108. The first section 108 can be closer to the proximal end 102 than the distal end 104. The first section 108 can have a first cross-sectional shape. The first section 108 can extend distally from the fastener section 106. The bone tie 100 can include a second section 110. The second section 110 can be closer to the proximal end 102 than the distal end 104. The second section 110 can have a second cross-sectional shape. The second section 110 can extend distally from the first section 108. The bone tie 100 can include a third section 112. The third section 112 can be closer to the distal end 104 than the proximal end 102. The third section 112 can have a third cross-sectional shape. The third section 112 can extend distally from the second section 110.

The bone tie 100 can include a neck section 114. The neck section 114 can be closer to the distal end 104 than the proximal end 102. The neck section 114 can taper from the third section 112 toward the distal end 104. The neck section 114 can extend distally from the third section 112. The neck section 114 can facilitate manipulation of the distal portion of the bone tie 100 by the bone tie inserter, as described herein. The neck section 114 can be shaped to interface with the bone tie inserter. The neck section 114 can be shaped to form a mechanical interfit or coupling as described herein.

The bone tie 100 can include a head section 116. The head section 116 can be located at or near the distal end 104. The neck section 114 can taper toward the head section 116. The head section 116 can extend distally from the neck section 114. The head section 116 can facilitate manipulation of the distal portion of the bone tie 100 by the bone tie inserter, as described herein. The head section 116 can be shaped to be grasped or cupped by the bone tie inserter. The head section 116 can be shaped to pivot and/or rotate relative to the bone tie inserter.

FIG. 2 is a perspective back view of the bone tie 100. The bone tie 100 can have a smooth surface along the first section 108, the second section 110, and the third section 112. The bone tie 100 can have a continuous surface along the first section 108, the second section 110, and the third section 112.

FIG. 3 illustrates a perspective view of a proximal portion of the bone tie 100. The bone tie can include the proximal end 102, the fastener section 106, first section 108, and the second section 110.

The fastener section 106 can include a lumen 118. The lumen 118 can be oriented perpendicular to a longitudinal axis 150 of the bone tie 100. The bone tie 100 can include a ratchet 122 disposed within the lumen 118. The ratchet 122 is configured to deflect to allow one or gears to travel through the lumen 118 in one direction, but limit or prevent travel in another direction. The fastener section 106 can form an enlarged end of the bone tie 100. The fastener section 106 can be generally rectangular or cuboid. The fastener section 106 can have a width larger than the first section 108. The fastener section 106 can have a thickness larger than the first section 108. The fastener section 106 can include rounded edges or corners. The fastener section 106 can have any shape to accommodate the ratchet 122 disposed therewithin. The fastener section 106 can have any shape to accommodate any fastener mechanism described herein.

The first section 108 can have the first cross-sectional shape. The first cross-sectional shape can be generally rectangular or cuboid. The first cross-sectional shape can have rounded edges or corners. The first section 108 can include a width and a thickness. The first section 108 can include a groove 124. The groove 124 can reduce the thickness of the first section 108. The groove 124 can taper from the fastener section 106. The groove 124 can taper to the second section 110.

The second section 110 can have the second cross-sectional shape. The second cross-sectional shape can be generally rectangular or cuboid. The second cross-sectional shape can have rounded edges or corners. The second section 110 can include a groove 126. The groove 124 of the first section 108 can extend to the groove 126 of the second section 110. The second section 110 can include one or more gears 128. The gears 128 can be ramped surfaces. The gears 128 can form a rack. The gears 128 can be wedge surfaces. The gears 128 can be inclined upward toward the proximal end 102. The gears 128 can be inclined downward toward the distal end 104. The gears 128 can be disposed within the groove 126 of the second section 110. The first section 108 and the second section 110 can include a constant width. The first section 108 and the second section 110 can include a constant thickness. The first section 108 and the second section 110 can include a constant thickness measured along the edges of the first section 108 and the second section 110.

FIG. 4 illustrates a perspective view of a distal portion of the bone tie 100. The bone tie can include the second section 110, the third section 112, the neck section 114, the head section 116, and the distal end 104.

The third section 112 can have a third cross-sectional shape. The third cross-sectional shape can be generally rectangular or cuboid. The third cross-sectional shape can have rounded edges or corners. In some embodiments, the first cross-sectional shape and the third cross-sectional shape are the same or similar. The third section 112 can include a width and a thickness. The third section 112 can include a groove 130. The groove 130 can reduce the thickness of the third section 112. The groove 130 can taper from the second section 110. The groove 130 can taper to the neck section 114.

Two or more of the first section 108, the second section 110, and the third section 112 can include a constant width. Two or more of the first section 108, the second section 110, and the third section 112 can include a constant thickness. Two or more of the first section 108, the second section 110, and the third section 112 can include a constant thickness measured along the edges of the respective sections. The bone tie 100 can have a constant width along a substantial portion of the length. The bone tie 100 can have a constant thickness along a substantial portion of the length.

FIG. 5 illustrates an enlarged view of the distal portion of the bone tie 100. The bone tie 100 can include the neck section 114. The neck section 114 tapers along the width. The neck section 114 tapers from a larger width near the third section 112 to a smaller width near the head section 116. The neck section 114 can include a groove 132. The groove 132 can reduce the thickness of the neck section 114. The groove 132 of the neck section 114 can extend from the groove 130 of the third section 112.

The neck section 114 can lie in a plane along the longitudinal axis 150 of the bone tie 100 or the neck section 114 can include a curve 134. The curve 134 can have a constant radius of curvature. Two or more of the first section 108, the second section 110, and the third section 112 can be planar. The bone tie 100 can lie in a plane along a substantial portion of the length. The curve 134 can extend from the plane of the bone tie. The curve 134 can extend upward from the grooves 124, 126, 130, 132 of the bone tie 100. The curve 134 can extend upward from the gears 128 of the second section 110. The curve 134 can extend away from the longitudinal axis 150 of the bone tie 100.

The bone tie 100 can include the head section 116. The head section 116 can include a head 136. The head 136 can be rounded. The head 136 can be spherical. The head 136 can extend to the distal end 104 of the bone tie 100. The head section 116 can include a flange 138. The flange 138 can be positioned on the head 136. The flange 138 can be a rounded bill that extends from the head 136. The flange 138 can include a first tapered surface 140 and a second tapered surface 142. The first tapered surface 140 and the second tapered surface 142 can have different slopes. The second tapered surface 142 can form a ledge by which the head section 116 or head 136 can be grasped. The first tapered surface 140 and the second tapered surface 142 extend to the neck section 114.

The bone tie 100 can include a marker 144. The marker 144 can facilitate visualization of the bone tie 100, or a portion thereof. In the illustrated embodiment, the head 136 can include the marker 144. The head 136 can include a bore 146. The bore 146 can extend from an edge of the head 136 inward toward or past the center of the head 136. The marker 144 can be disposed within the bore 146. The marker 144 can be a radiopaque marker. The marker 144 can be formed of a metal or other radiopaque material. The marker 144 can identify the distal end 104 of the bone tie 100. In some embodiments, the bone tie 100 comprises a non-radiopaque material. In some embodiments, one or more radiopaque markers may be embedded in or on the bone tie 100 to assist in placement or monitoring of the bone tie 100 under radiographic visualization.

The bone tie 100 can be a flexible fastening band. The bone tie 100 can include the proximal end portion 102 and the distal end portion 104. In some embodiments, the head section 116 can be removed. The neck section 114 can be advanced through the lumen 118. When the neck section 114 is advanced, the ratchet 122 can extend into the groove 132. The third section 112 can be advanced through the lumen 118. When the third section 112 is advanced, the ratchet 122 can extend into the groove 130. The second section 110 can be advanced through the lumen 118. When the second section 110 is advanced, the ratchet 122 can extend into the groove 126. The ratchet 122 can engage the gears 128. The ratchet 122 can allow the second section 110 to travel through the lumen 118 in one direction, but limit travel through the lumen 118 in the opposite direction.

The bone tie 100 can be configured for altering the motion at the facet joints of the vertebral column. In some embodiments, the bone tie 100 can prevent motion of the facet joint. In some embodiments, the bone tie 100 can limit or reduce motion of the facet joint. In some embodiments, the bone tie 100 can limit motion to a range depending on the tightening of the loop of the bone tie 100. In some methods of use, the bone tie promotes fusion of the facet joints.

The bone tie 100 can be configured for altering the spacing at the facet joints of the vertebral column. In some embodiments, the bone tie 100 can reduce the spacing. In some embodiments, the bone tie 100 can maintain the anatomical spacing. The bone tie 100 can be a retaining member for anchoring a prosthesis or implant within the facet joint. In some embodiments, the bone tie 100 can pass through a central opening of the prosthesis or implant when the prosthesis or implant is inserted within the facet joint space. The bone tie 100 can be adapted for securing the location of the prosthesis or implant with respect to at least one of the articular surfaces.

The prosthesis or implant can have any shape or configuration. The prosthesis or implant can be substantially disc shaped. The first side of the prosthesis or implant can be concave, convex, or flat. The second side of the prosthesis or implant can be concave, convex, or flat. The shape can be determined based on a shape of a bone portion that the first side and the second side are configured to contact. In some embodiments, the prosthesis or implant fits entirely within the joint disc space. The prosthesis or implant can include any biocompatible material, e.g., stainless steel, titanium, PEEK, nylon, etc.

The bone tie 100 can have a width of 0.5 mm, 1 mm, 1.5 mm, 2 mm, 2.5 mm, 3 mm, 3.5 mm, 4 mm, or any range of the foregoing values. The width of the bone tie 100 can vary along the length of the bone tie 100. The bone tie 100 can have a thickness of 0.5 mm, 1 mm, 1.5 mm, 2 mm, 2.5 mm, 3 mm, 3.5 mm, 4 mm, or any range of the foregoing values. The thickness of the bone tie 100 can vary along the length of the bone tie 100. The bone tie 100 can have a length of 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, or any range of the foregoing values. For example, the bone tie 100 can have a length of 175 mm. In some embodiments, the second section 110 or the gears 128 can have a length of 5 mm, 10 mm, 15 mm, 20 mm, 25 mm, 30 mm, 35 mm, 40 mm, 45 mm, 50 mm, 60 mm, 65 mm, 70 mm, 75 mm, 80 mm, or any range of the foregoing values.

The bone tie 100 can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the materials described herein. The bone tie 100 can include any biocompatible material, e.g., stainless steel, titanium, PEEK, nylon, etc. In some embodiments, the bone tie 100 comprises at least two materials. The bone tie 100 can include a reinforcement piece disposed within the bone tie 100. By selecting a particular configuration and the one or more materials for the bone tie 100, the bone tie 100 can be designed to have the desired flexibility and resiliency.

In some embodiments, the bone tie 100 can form a unitary structure. The bone tie 100 can be integrally formed from the proximal end 102 to the distal end 104. In some embodiments, the bone tie 100 can include one or more unitarily formed sections along the length of the bone tie 100. One or more of the fastener section 106, the first section 108, the second section 110, the third section 112, the neck section 114, and the head section 116 can be unitarily formed. In some embodiments, the bone tie 100 can include one or more separately formed sections along the length of the bone tie 100. One or more of the fastener section 106, the first section 108, the second section 110, the third section 112, the neck section 114, and the head section 116 can be separately formed. In some embodiments, the marker 144 is separately formed. In some embodiments, the bone tie 100 can form a monolithic structure. The bone tie 100 can be monolithically formed or separately formed. The bone tie 100 can be formed of the same or similar material. The sections of the bone tie 100 can be formed of the same or similar construction. In some embodiments, the bone tie 100 is formed from an injection molding process.

In some embodiments, the shape of the first section 108, the second section 110, and/or the third section 112 can be determined based on the shape of an artificial lumen formed through an articular process of a vertebra. In some embodiments, the shape of the artificial lumen is cylindrical, the shape of the head 136 can be rounded or spherical to allow the head 136 to slideably advance through the artificial lumen. In some embodiments, the shape of the artificial lumen has a cross-sectional dimension or diameter greater than the cross-sectional dimension or diameter of the head 136 to allow the head 136 to slideably advance through the artificial lumen. The head 136 can have a larger cross-sectional dimension or diameter than the first section 108, the second section 110, the third section 112, and the neck section 114 to allow the first section 108, the second section 110, the third section 112, and the neck section 114 to easily slide within the artificial lumen.

In some embodiments, the characteristic of the bone tie 100 can vary along the length of the bone tie 100. The characteristics can vary between one or more of the fastener section 106, the first section 108, the second section 110, the third section 112, the neck section 114, and the head section 116. In some embodiments, each section has different characteristics. In some embodiments, the flexibility of the bone tie 100 varies along the length of the bone tie 100. In some embodiments, the torsional strength of the bone tie 100 varies along the length of the bone tie 100. In some embodiments, the resistance to deformation or elongation of the bone tie 100 varies along the length of the bone tie 100. In some embodiments, the characteristic of the bone tie 100 vary based, at least in part, on the shape of the various sections.

In some embodiments, the characteristic of the bone tie 100 vary based on the material of the various sections. In some embodiments, the characteristic of the bone tie 100 vary along the length based, at least in part, on a reinforcement piece. The reinforcement piece can be separately formed from or integrally formed with the bone tie 100. The reinforcement piece can comprise a different material or material property. In some embodiments, the reinforcement piece is disposed within a section of the bone tie 100. The reinforcement piece can be disposed within the fastener section 106, the first section 108, the second section 110, the third section 112, the neck section 114, the head section 116, any combination of the foregoing, or disposed only within one or more sections of the foregoing. The reinforcement piece can increase the strength of a section of the bone tie 100. In some embodiments, the reinforcement piece has a substantially uniform shape. The shape, material, or other characteristics of the reinforcement piece can be selected depending on the desired bending and/or torsion characteristics of the material chosen. The reinforcement piece can increase or decrease bending strength. The reinforcement piece can increase or decrease torsion strength. Any shape, material, or other property of the reinforcement piece can be selected to achieve the desired bending and/or torsion strength of the bone tie 100. In some embodiments, the reinforcement piece is radiopaque. In some embodiments, the reinforcement piece is radiolucent.

3. Bone Tie Advancer

Figure 6:
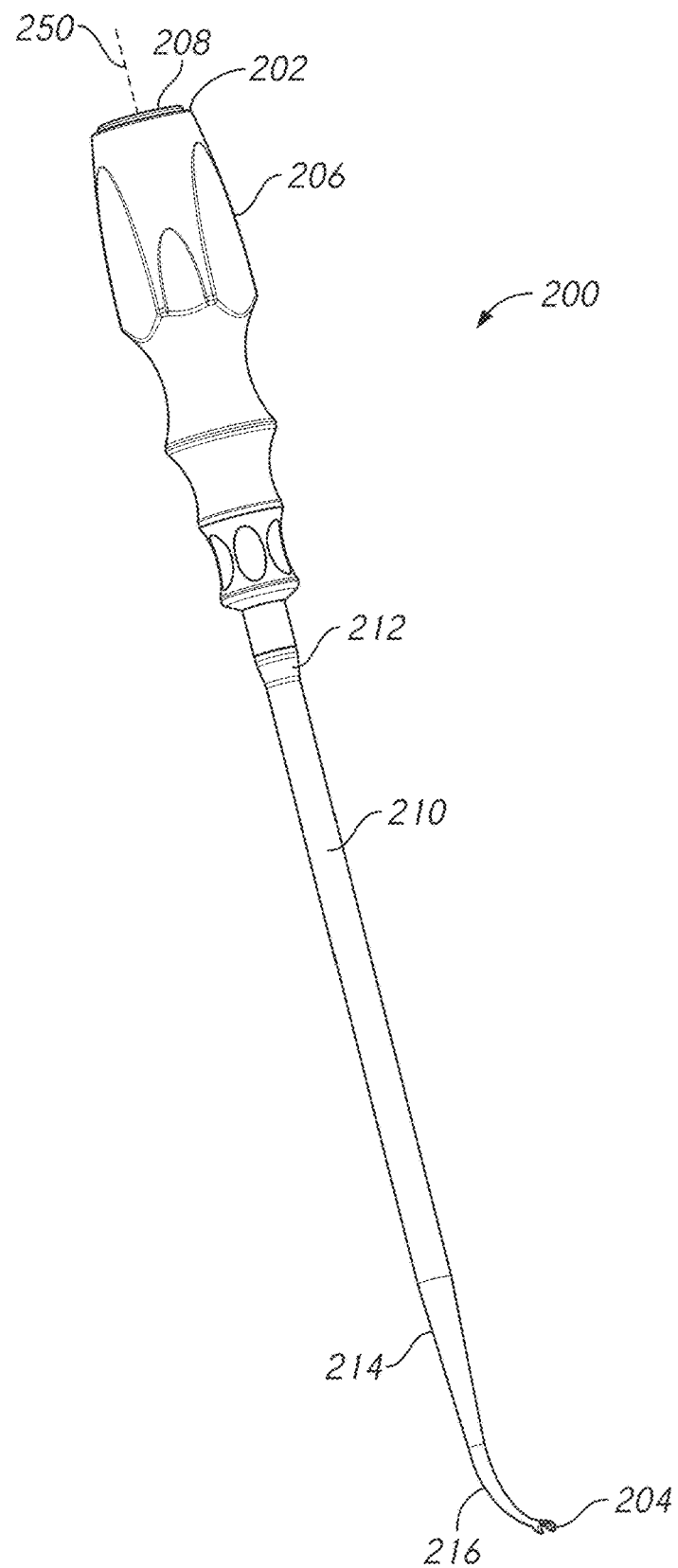
FIG. 6 is a perspective front view of an embodiment of a bone tie advancer.
Figure 7:
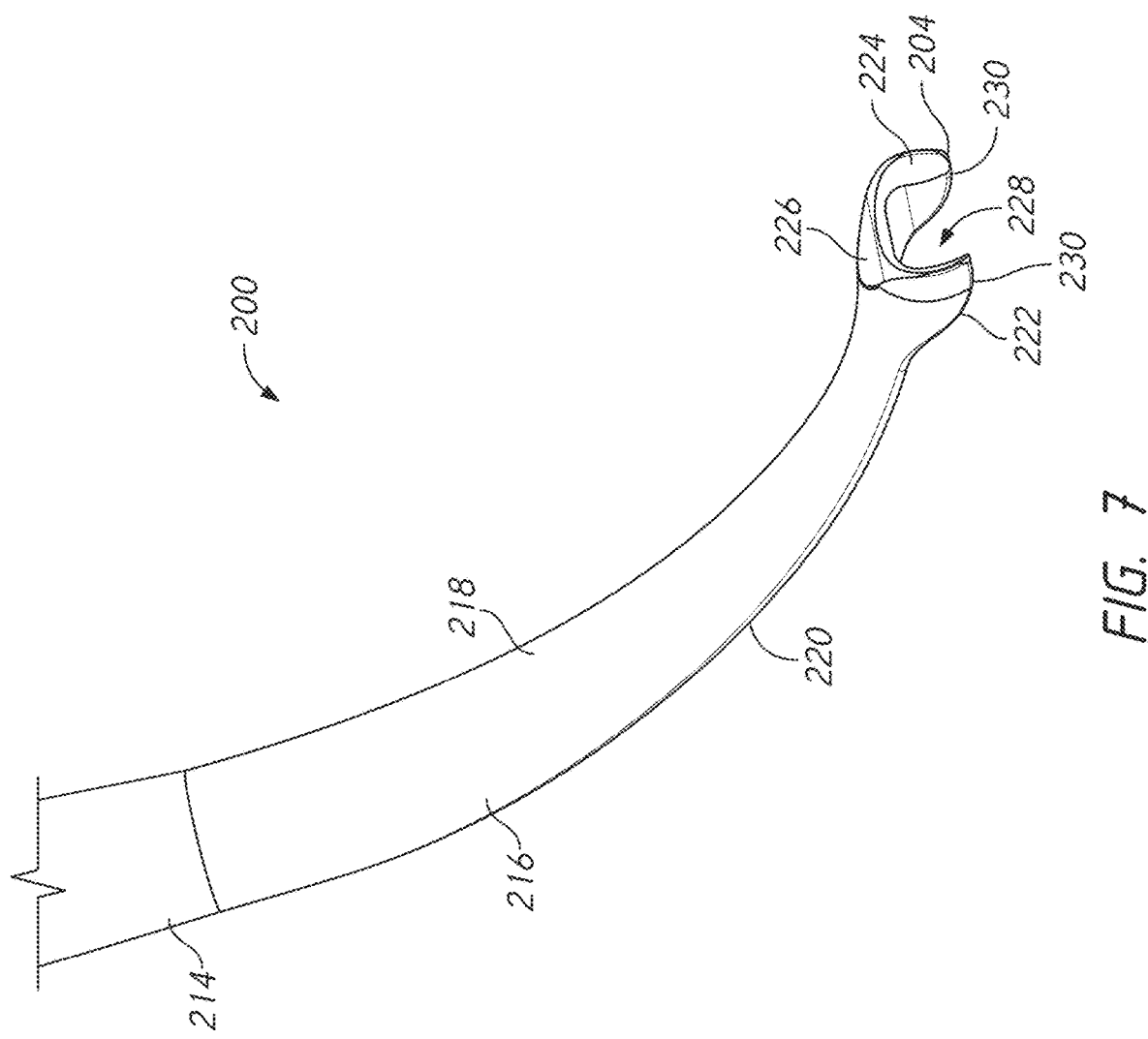
FIG. 7 is a perspective front view of a distal portion of the bone tie advancer of FIG. 6.
Figure 8:
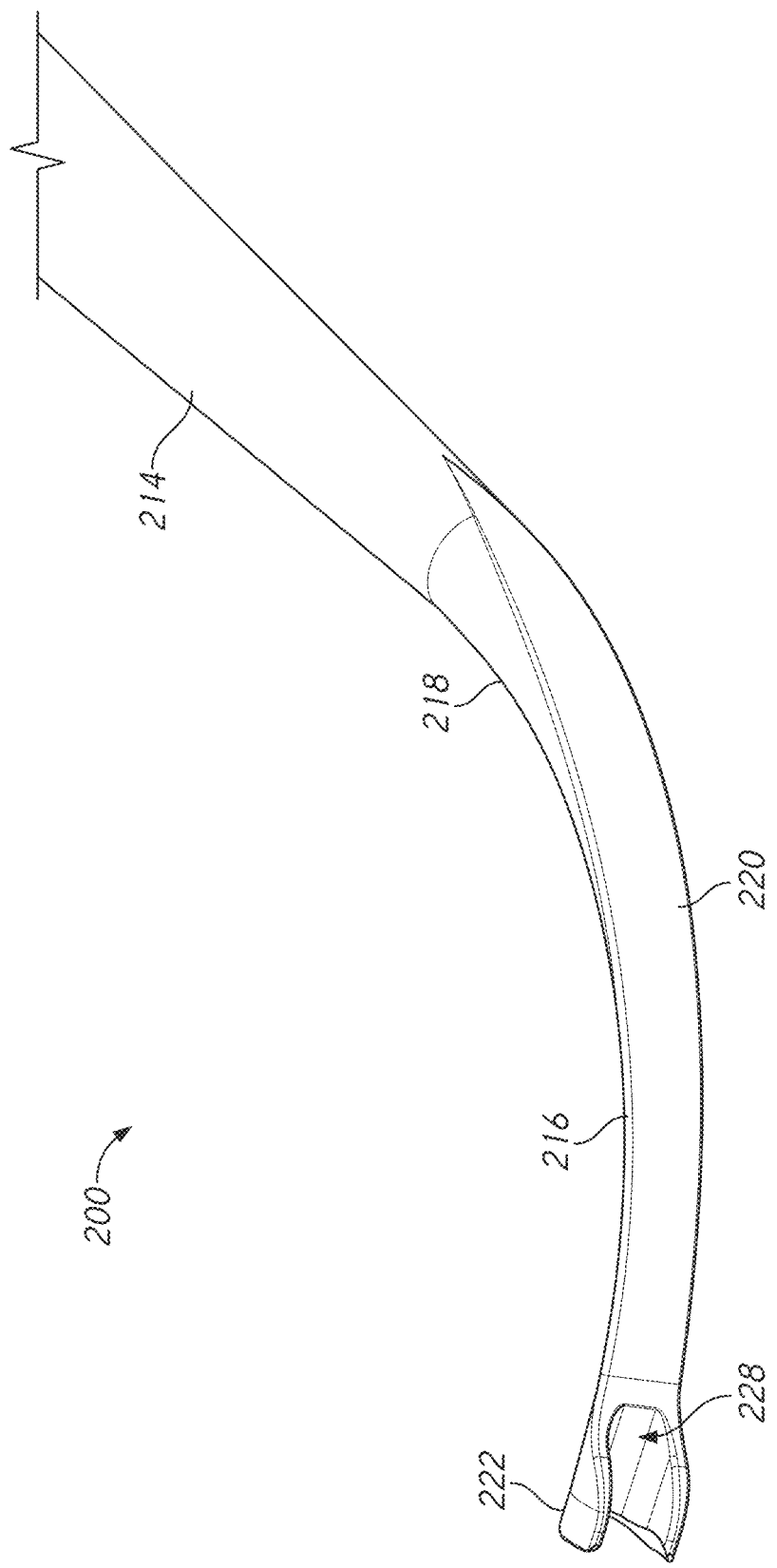
FIG. 8 is a perspective back view of a distal portion of the bone tie advancer of FIG. 6.

FIGS. 6-8 depict views of an embodiment of a bone tie advancer 200. FIG. 6 illustrates a perspective front view. FIG. 7 illustrates a perspective front view of a distal portion. FIG. 8 illustrates a perspective back view of a distal portion. The bone tie advancer 200 can include a proximal end 202 and a distal end 204.

The bone tie advancer 200 can include a proximal handle 206. The proximal handle 206 can be any shape configured to be gripped by the user. The proximal handle 206 can include one or more grooves designed to accommodate the fingers of the user. The proximal handle 206 can be shaped for right-handed use, left-handed use, or ambidextrous use. The proximal handle 206 can include an impact cap 208. The impact cap 208 can have a flat proximal end to allow a force to be applied.

The bone tie advancer 200 can include a shaft 210. The shaft 210 can extend distally from the proximal handle 206. The shaft 210 can include an upper portion 212. The upper portion 212 can be cylindrical. The upper portion 212 can have one or more cylindrical sections of varying diameters. The upper portion 212 can include a stepped surface. The upper portion 212 can have any cross-sectional shape including round, square, rectangular, polygonal, oval, or any other shape. The upper portion 212 can be an elongate member. The upper portion 212 can lie along a longitudinal axis 250.

The shaft 210 can include a tapered portion 214. The tapered portion 214 can be distal to the upper portion 212 of the shaft 210. The tapered portion 214 can have a narrower cross-section toward the distal end 204. The tapered portion 214 can be frusto-conical. The tapered portion 214 can have a reduced cross-section relative to the upper portion 212 of the shaft 210 to enable the shaft 210 to be positioned relative to the patient's anatomy. The tapered portion 214 can lie along the longitudinal axis 250. The tapered portion 214 can taper inward relative to the longitudinal axis 250. The upper portion 212 and the tapered portion 214 can be coaxial.

The shaft 210 can include a curved portion 216. The curved portion 216 can be distal to the tapered portion 214 of the shaft 210. The curved portion 216 can have a substantially constant width. The curved portion 216 can have a reduced cross-section relative to the upper portion 212 of the shaft 210 to enable the shaft 210 to be positioned relative to the patient's anatomy. The curved portion 216 can be shaped to be inserted within the artificial lumen of the bone portions. The curved portion 216 can be shaped according to the lumen-forming tool that creates the lumen in the bone portions. The curved portion 216 can have a constant radius of curvature. The curved portion 216 can curve away from the longitudinal axis 250 of the upper portion 212. The curved portion 216 can extend laterally from the longitudinal axis 250 of the upper portion 212.

FIGS. 7 and 8 are enlarged views of the distal portion of the bone tie advancer 200. The curved portion 216 can include a rounded surface 218. The rounded surface 218 can extend distally from the tapered portion 214. The rounded surface 218 can be proximal-facing. The shaft 210 can include a planar surface 220. The planar surface 220 can be distal-facing. The planar surface 220 can form the outside curve of the curved portion 216. The rounded surface 218 can form the inside curve of the curved portion 216. The planar surface 220 can extend along at least a portion of the curved portion 216. The planar surface 220 can extend along at least a portion of the tapered portion 214.

The shaft 210 can include an advancer portion 222. The advancer portion 222 can be configured to interface with the bone tie 100. The advancer portion 222 can be located at or near the distal end 204 of the bone tie advancer 200. The advancer portion 222 can include a curved surface 224. The curved surface 224 can correspond to the curvature of the head 136. The curved surface 224 can cup the head 136. The curved surface 224 can curve around the distal-facing portion of the head 136. The curved surface 224 can allow the force of the bone tie advancer 200 to be transferred to the head 136. The curved surface 224 can allow movement of the bone tie advancer 200 to be transferred to the head 136. The curved surface 224 can form the distal end 204 of the bone tie advancer 200. The advancer portion 222 can include a tapered surface 226. The tapered surface 226 can be proximal-facing. The tapered surface 226 can allow visualization and clearance relative to the patient's anatomy. The advancer portion 222 can include retaining arms 230. The retaining arms 230 can extend proximally from the curved surface 224 and can be separately formed from or integrally formed with the curved surface 224. The retaining arms 230 can engage the flange 138. The retaining arms 230 can engage the second tapered surface 142 of the flange 138. The retaining arms 230 can engage the neck section 114. The interior portion of the retaining arms 230 can be rounded, tapered, or any other shape corresponding to the flange 138, second tapered surface 142 and/or neck section 114. The retaining arms 230 can facilitate secure engagement of the bone tie 100 for insertion of the bone tie 100 within the artificial lumen of the bone portions.

The advancer portion 222 can include a channel 228. The channel 228 can correspond to the shape of the neck section 114 of the bone tie 100. The neck section 114 of the bone tie 100 can be disposed within the channel 228 when the curved surface 224 abuts the head 136. The channel 228 can be formed by three sides. The three sides can include rounded edges. The three sides can have any shape to accept the bone tie 100. The channel 228 can include an open side. The open side can be distal-facing. The channel 228 can surround a portion of the neck section 114 of the bone tie 100. When the neck section 114 of the bone tie 100 is disposed within the channel 228, the curved surface 224 can align and abut the head 136. The channel 228 can increase the contact between the advancer portion 222 and the bone tie 100.

4. Bone Tie Retriever

Figure 9:
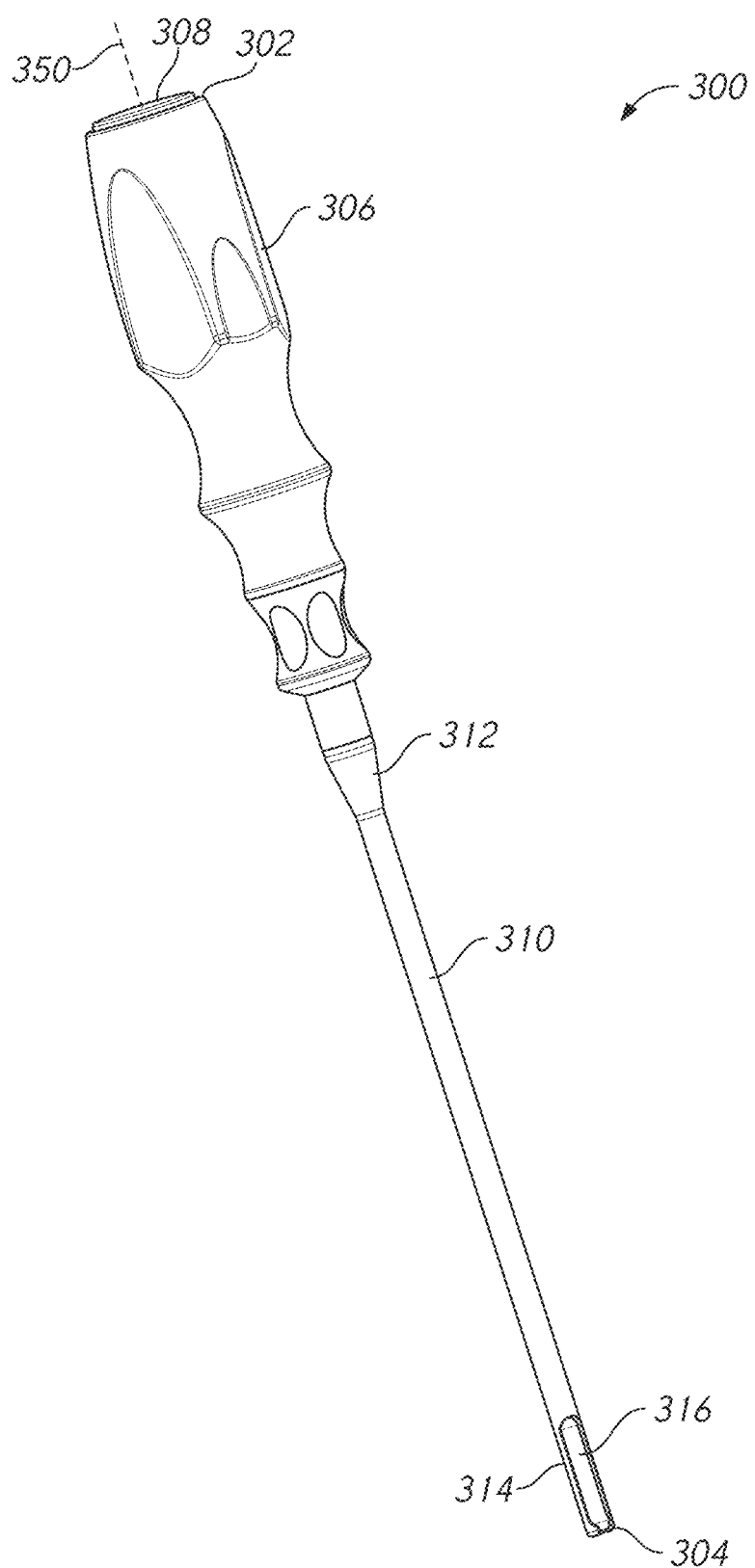
FIG. 9 is a perspective front view of an embodiment of a bone tie retriever.
Figure 10:
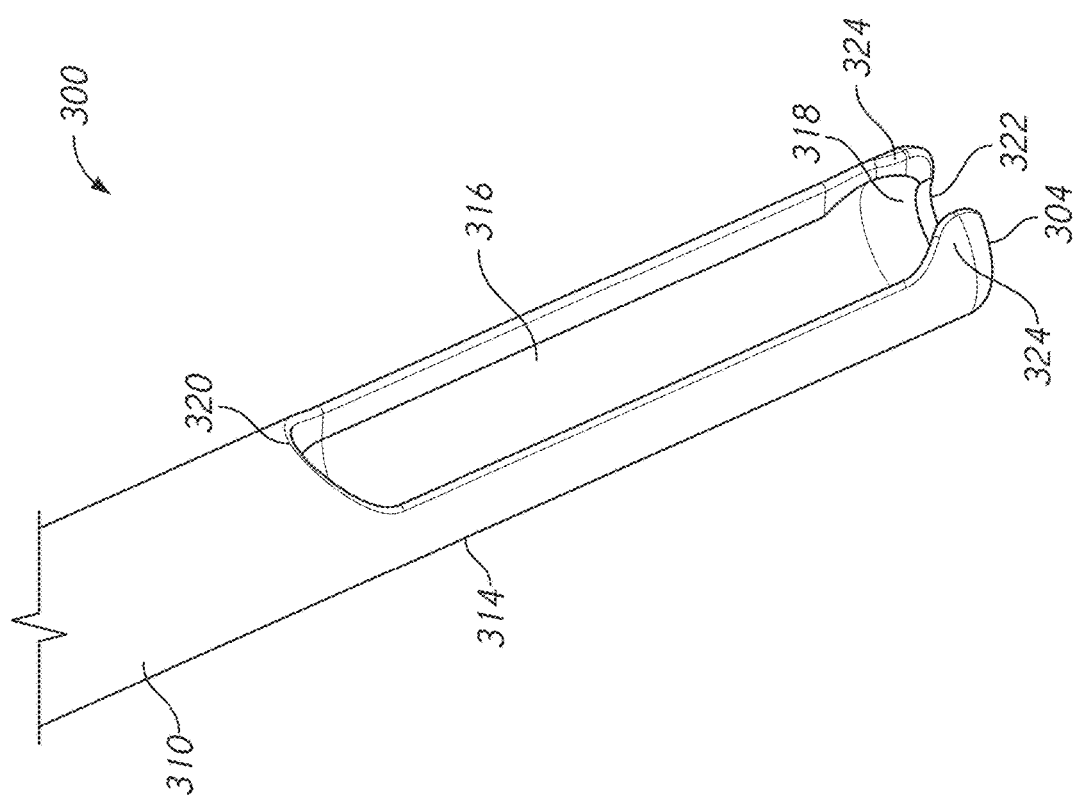
FIG. 10 is a perspective front view of a distal portion of the bone tie retriever of FIG. 9.
Figure 11:
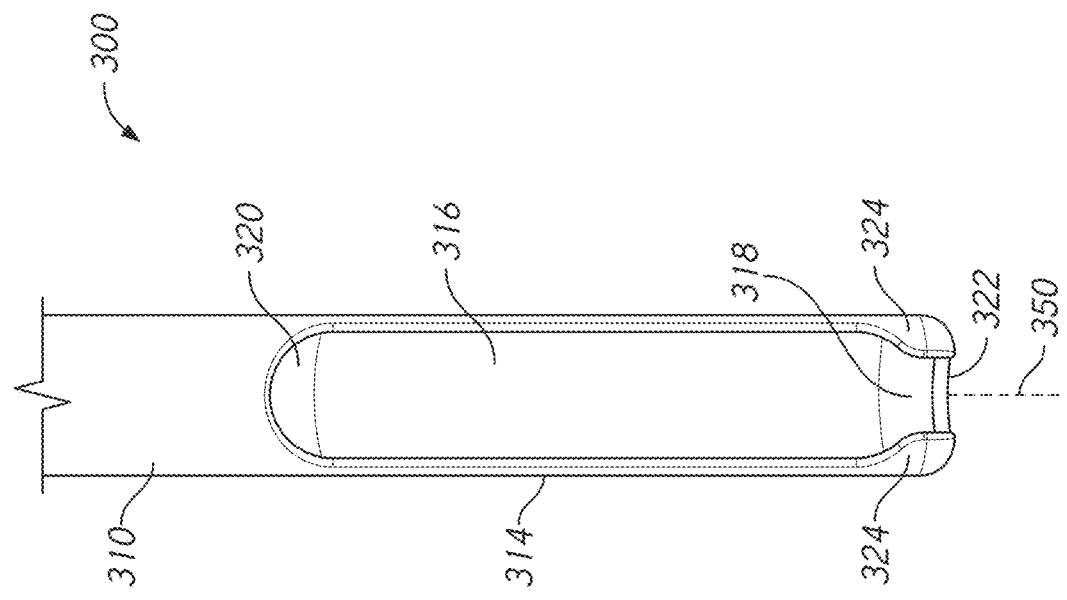
FIG. 11 is a front view of a distal portion of the bone tie retriever of FIG. 9.
Figure 12:
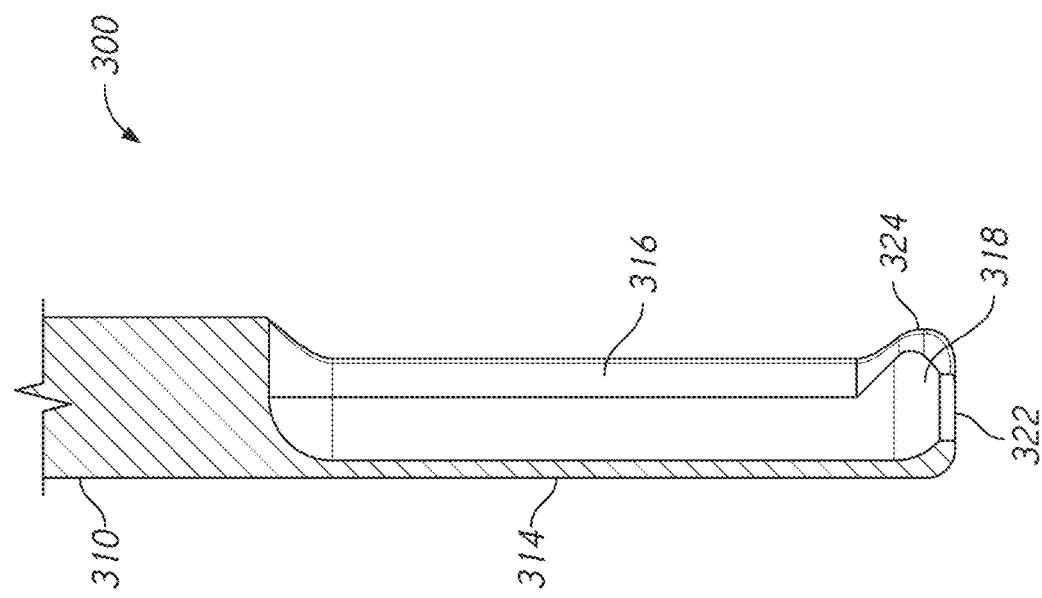
FIG. 12 is a cross-sectional view of the distal portion of the bone tie retriever of FIG. 9.
Figure 13:
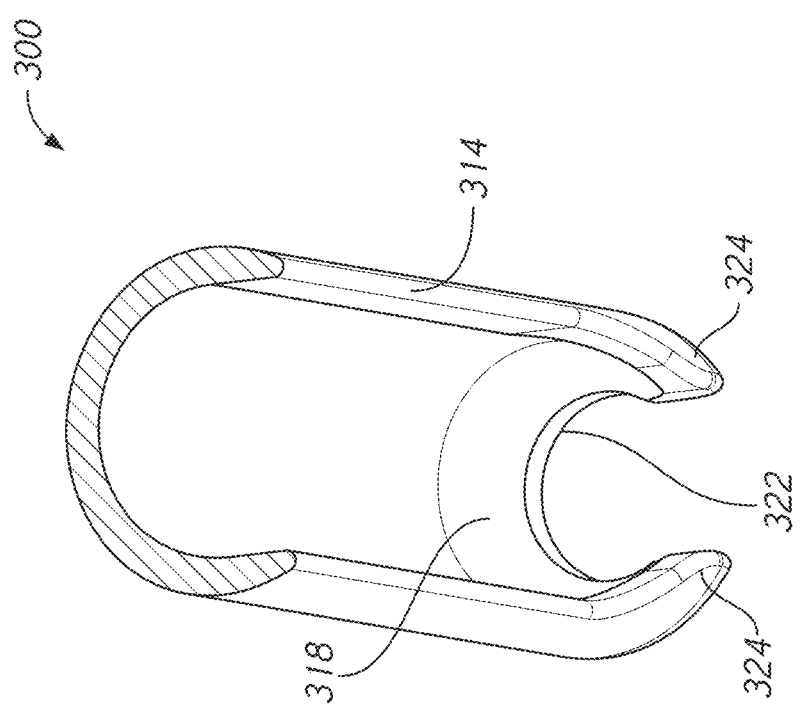
FIG. 13 is a cross-sectional view of the distal portion of the bone tie retriever of FIG. 9.

FIGS. 9-13 depict views of an embodiment of a bone tie retriever 300. FIG. 9 illustrates a perspective front view. FIG. 10 illustrates a perspective front view of a distal portion. FIG. 11 illustrates a front view of a distal portion. FIG. 12 illustrates a cross-sectional view of the distal portion. FIG. 13 illustrates a cross-sectional view of the distal portion. The bone tie retriever 300 can include a proximal end 302 and a distal end 304.

The bone tie retriever 300 can include a proximal handle 306. The proximal handle 306 can be any shape configured to be gripped by the user. The proximal handle 306 can include one or more grooves designed to accommodate the fingers of the user. The proximal handle 306 can be shaped for right-handed use, left-handed use, or ambidextrous use. The proximal handle 306 can include an impact cap 308. The impact cap 308 can have a flat proximal end to allow a force to be applied. The proximal handles 206, 306 can be the same or similar. The proximal handles 206, 306 can be mirror images. In some embodiments, the proximal handle 206 can be designed for use with the right hand of the user and the proximal handle 306 can be designed for use with the left hand of the user. The proximal handles 206, 306 can be different. The proximal handles 206, 306 can include a different visual indicator to indicate the different functions of the bone tie advancer 200 and the bone tie retriever 300. In some embodiments, the proximal handles 206, 306 can be different colors or include a visual marking.

The bone tie retriever 300 can include a shaft 310. The shaft 310 can extend distally from the proximal handle 306. The shaft 310 can include an upper portion 312. The upper portion 312 can be cylindrical. The upper portion 312 can have one or more cylindrical sections of varying diameters. The upper portion 312 can include a stepped surface. The upper portion 312 can have any cross-sectional shape including round, square, rectangular, polygonal, oval, or any other shape. The upper portion 312 can be an elongate member. The upper portion 312 can lie along a longitudinal axis 350. The upper portions 212, 312 can be the same or substantially similar. The shaft 310 can include a retriever portion 314. The retriever portion 314 can be distal to the upper portion 312 of the shaft 310.

FIG. 10 illustrates an enlarged view of a distal portion of the bone tie retriever 300. The retriever portion 314 can be shaped to receive the head 136 of the bone tie 100. The retriever portion 314 can include a channel 316. The channel 316 can include a rounded portion 320. The rounded portion 320 can include a curvature corresponding to the head 136 of the bone tie 100. The channel 316 can be concave along the longitudinal axis 350.

The channel 316 can include a ledge 318. The ledge 318 can be flat, curved, or tapered. The ledge 318 can include a curvature that corresponds to the curvature of the head 136. The ledge 318 can be dimensioned to allow for pivotal and/or rotational movement of the head 136 within the channel 316. In some embodiments, the ledge 318 can have a curved or poly-axial surface configured to accept the head 136. In some embodiments, the ledge 318 can be concave. In some embodiments, the ledge 318 can have a concavity that corresponds to a convexity of the head 136. The concavity of the ledge 318 can allow the head 136 to pivot and/or rotate while still retaining the head 136 within the channel 316. The ledge 318 can allow the head 136, and thus the bone tie 100, to pivot 10°, 20°, 30°, 40°, 50°, 60°, 70°, 80°, 90°, 100°, 110°, 120°, 130°, 140°, 150°, 160°, 170°, 180°, or any range of the foregoing values. In particular embodiments, the ledge 318 can allow the head 136, and thus the bone tie 100, to pivot 60°, 70°, 80°, 90°, or any range of the foregoing values. The ledge 318 can allow the head 136 to abut and rotate against the ledge 318.

The retriever portion 314 can include an opening 322. The opening 322 can be located at or near the distal end 304. The ledge 318 surrounds the opening 322. The ledge 318 can be shaped to allow the neck section 114 to pass through the opening 322. The ledge 318 can be shaped to prevent the head 136 from passing through the opening 322. The ledge 318 can be sized according to the corresponding bone tie 100.

The retriever portion 314 can include one or more retention features 324. In the illustrated embodiment, the retriever portion 314 includes two retention features 324. The one or more retention features 324 narrow the channel 316 near the distal end 304. The channel 316 extends through the one or more retention features 324. The one or more retention features 324 can be disposed near the ledge 318. The one or more retention features 324 can function to retain the head 136 when the head 136 is seated against the ledge 318.

In some embodiments, the channel 316 may be dimensioned to allow entry of the head 136, or the head 136 and neck section 114, in generally one particular orientation. In some embodiments, the channel 316 may be dimensioned to allow entry of the head 136, or the head 136 and neck section 114, in a range of orientations. In some embodiments, the channel 316 may be dimensioned to allow entry of the head 136 wherein the neck section 114 is generally perpendicular to the longitudinal axis 350 of the shaft 310. In some embodiments, the channel 316 may be dimensioned to allow retention of the head 136 wherein the neck section 114 is generally parallel to or coaxial with the longitudinal axis 350. In some embodiments, the channel 316 is configured to allow the neck section 114 to pass between the one or more retention features 324. In some embodiments, the retriever portion 314 is configured to allow the neck section 114 to pivot, or pivot and rotate, from extending between the one or more retention features 324 to extending into the opening 322. In some embodiments, the retriever portion 314 is configured to allow the neck section 114 to pivot, or pivot and rotate, from the opening 322 to the channel 316. In some embodiments, the channel 316 is configured to prevent or limit the head 136 from passing between the one or more retention features 324.

5. Methods of Use

Figure 14:
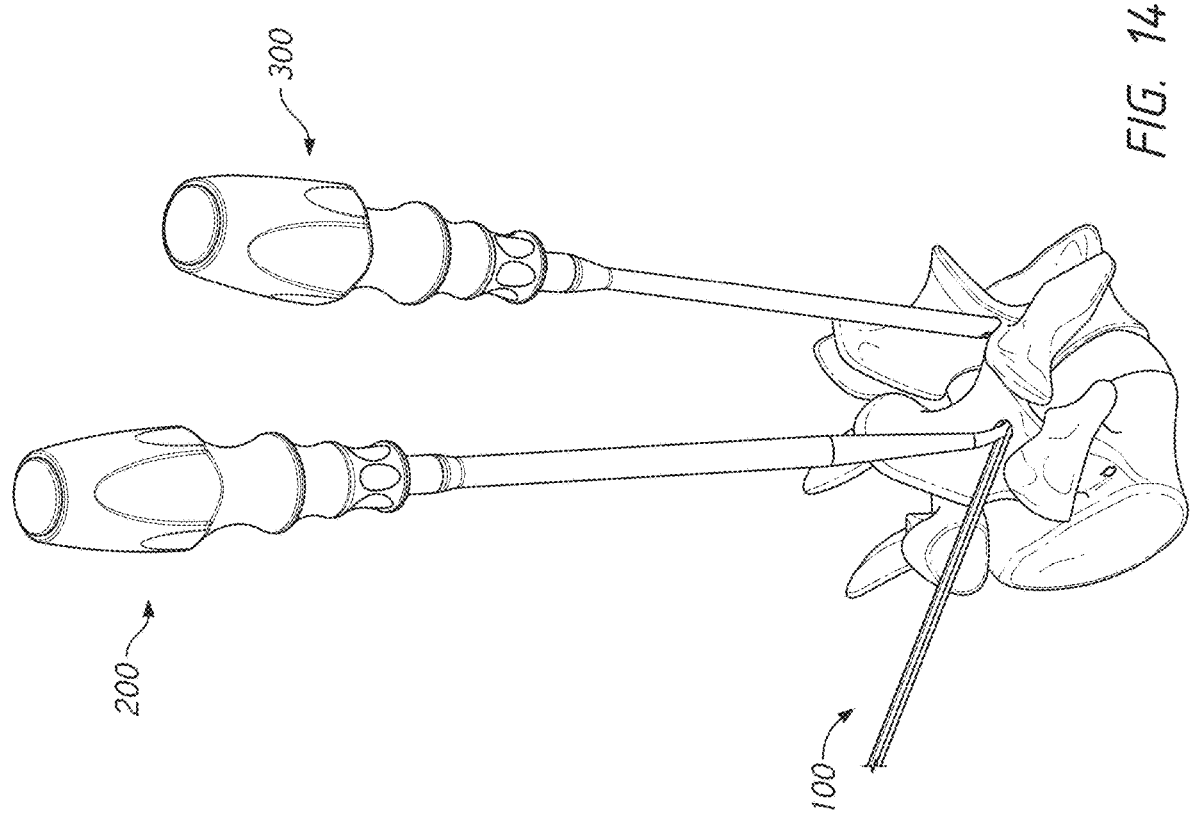
FIG. 14 is a view of the bone tie of FIG. 1, the bone tie advancer of FIG. 6, and the bone tie retriever of FIG. 9 within the vertebrae.
Figure 15:
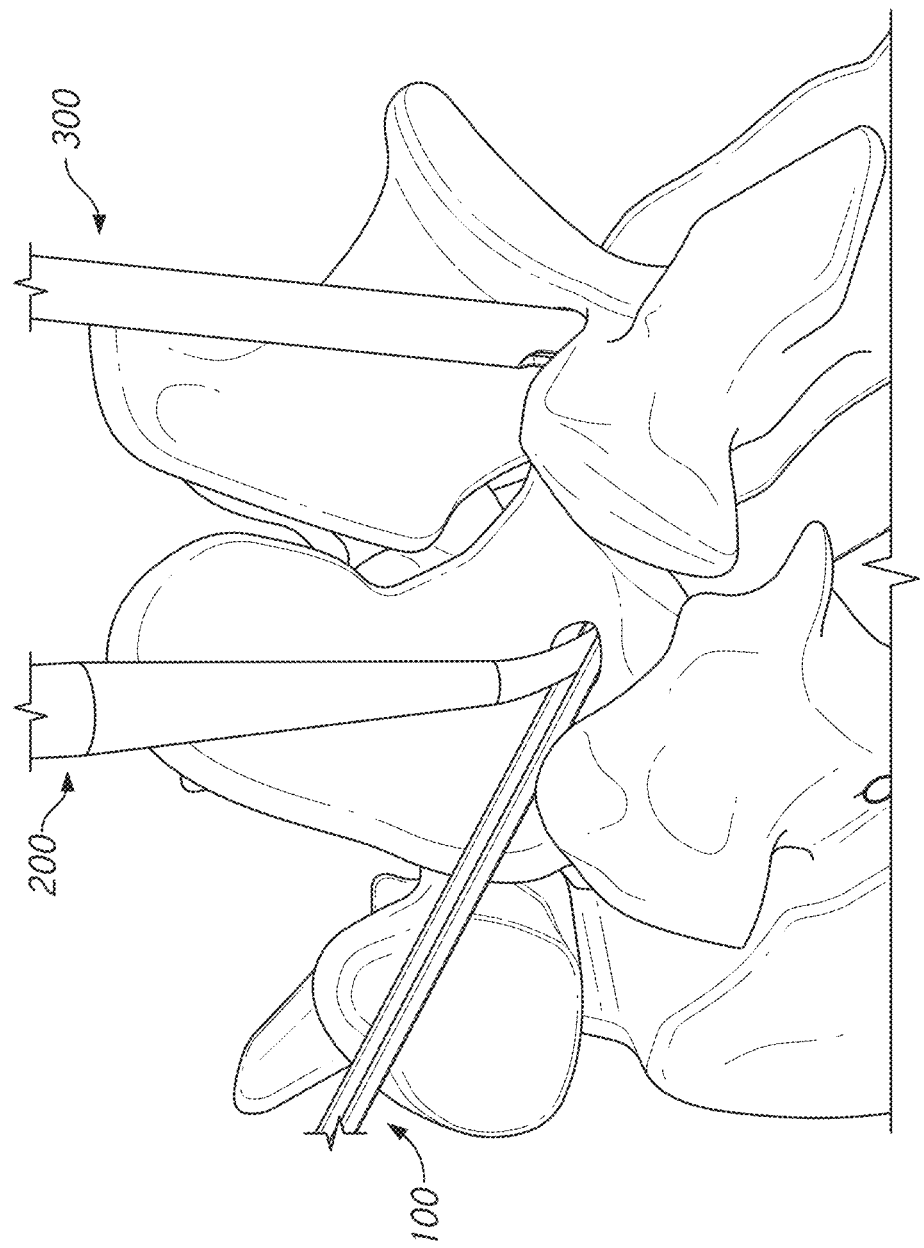
FIG. 15 is an enlarged view of FIG. 14.
Figure 16:
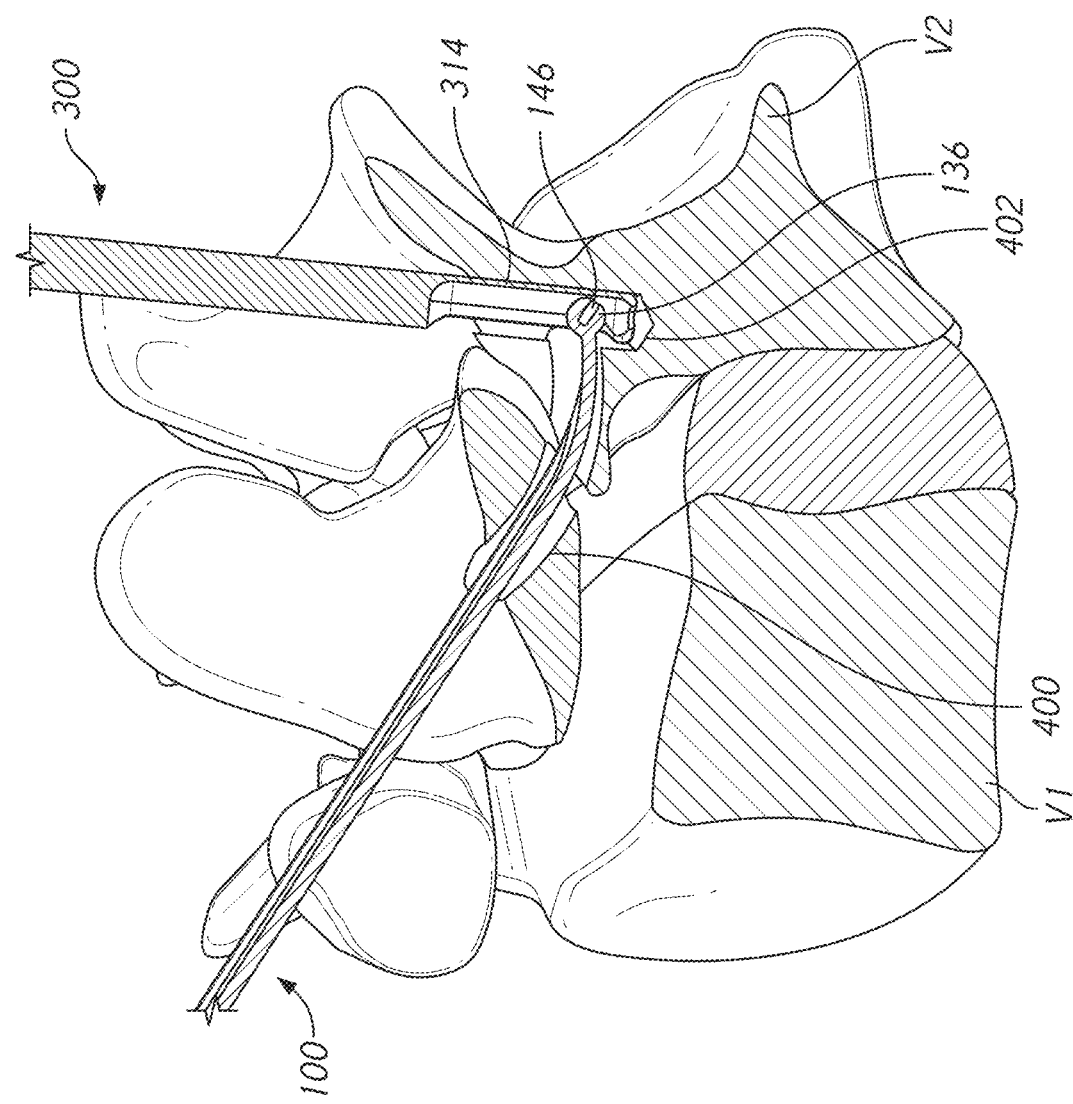
FIG. 16 is a cross-sectional view of the bone tie of FIG. 1 and the bone tie retriever of FIG. 9 within the vertebrae.

FIGS. 14 and 15 illustrate the bone tie 100, the bone tie advancer 200, and the bone tie retriever 300 in relation to vertebrae during methods of use. FIGS. 14 and 15 illustrate the bone tie 100, the bone tie advancer 200, and the bone tie retriever 300. The proximal ends are visible and the distal ends are disposed within lumens in the vertebrae. FIG. 15 is a close-up view of FIG. 14. FIG. 16 is a cross-sectional view illustrating a placement of the bone tie 100 and the bone tie retriever 300 in relation to the vertebrae.

The bone tie 100 can be configured to stabilize or fuse adjacent vertebrae. The bone tie 100 can be used to fuse a vertebra V1 and vertebra V2 via the inferior articular process IAP1A of vertebra V1 and the superior articular process SAP2A of vertebra V2. In some methods of use, a second bone tie 100 can be used to fuse a vertebra V1 and vertebra V2 via the inferior articular process IAP1B of vertebra V1 and the superior articular process SAP2B of vertebra V2. In some embodiments, vertebra V1 and vertebra V2 are fused using only one of bone tie 100. In some embodiments, one bone tie 100 can be used to stabilize vertebra V1 and vertebra V2 via one of the inferior articular process IAP1A of vertebra V1 and the superior articular process SAP2A of vertebra V2, or, via the inferior articular process IAP1B of vertebra V1 and the superior articular process SAP2B of vertebra V2. In some embodiments, two bone ties 100 can be used to stabilize vertebra V1 and vertebra V2 via both of the inferior articular process IAP1A of vertebra V1 and the superior articular process SAP2A of vertebra V2, and, the inferior articular process IAP1B of vertebra V1 and the superior articular process SAP2B of vertebra V2. The methods described herein can be repeated for any pair of an inferior articular process and a superior articular process.

In some methods of use, a lumen is formed through the articular processes. The lumen can be formed with a lumen-forming tool, such as a drill, tissue punch, or reamer. The lumen is formed through one or more articular processes of the vertebrae to facilitate implantation of the bone tie 100. In some embodiments, at least a portion of the lumen has a curved or non-linear configuration. In some embodiments, at least a portion of the lumen has a straight or linear configuration. In some methods of use, two or more lumens are formed. A drill or other device can be used to form a lumen in superior articular process SAP of vertebra V2 and inferior articular process IAP of vertebra V1. Specifically, the drill can be used to form the lumen in a facet of superior articular process SAP of vertebra V2 and to form the lumen in a facet of inferior articular process IAP of vertebra V1. In some embodiments, one lumen-forming tool forms one or more lumens. In some embodiments, two lumen-forming tools are utilized to form two lumens.

In some methods of use, a portion of the surface of the facet of SAP and IAP can be prepared for fusion. In some methods of use, a portion of the surface of the facet can be ground, scored, roughened, or sanded, such that the surface of the facet can better adhere to any substances to aid in fusion and/or otherwise fuse more readily to an implant or prosthesis. In some methods of use, the surgical procedure can include preparing the area near and/or around the vertebra by, for example, removing all or a portion of ligaments, cartilage, and/or other tissue. In some methods of use, the area near and/or around a facet joint can be prepared by removing all or a portion of the facet joint capsule. The implant or prosthesis, if provided, can be inserted between the superior articular process SAP of vertebra V2 and inferior articular process IAP of vertebra V1.

FIG. 16 illustrates a cross-sectional view of the vertebrae. The bone tie 100, the bone tie advancer 200 (not shown in FIG. 16), and the bone tie retriever 300 can be located within lumens as described herein. The first lumen 400 can be curved. The first lumen 400 can extend from a first vertebra toward a second vertebra. The first lumen 400 can extend through the facet joint space. The second lumen 402 can be straight. The second lumen 402 can extend downward from a surface of the second vertebra. The second lumen 402 can extend only through the second vertebra. The second lumen 402 can intersect the first lumen 400.

The bone tie 100 can be positioned within and adjacent to the bone tie advancer 200. As the bone tie advancer 200 is moved by the user, the head section 116 and the neck section 114 is correspondingly moved. The bone tie 100 can be advanced through the first lumen 400 by the bone tie advancer 200. The bone tie 100 can be advanced through the facet joint space by the bone tie advancer 200. The bone tie 100 can be advanced through at least a portion of the second lumen 402 by the bone tie advancer 200. In some embodiments, the bone tie 100 and the bone tie advancer 200 can have a bend or curve to facilitate directing the head 136 of the bone tie 100 into the lumen 400. In some embodiments, the bone tie 100 and the bone tie advancer 200 can have a bend or curve corresponding to the curvature of the first lumen 400. The bone tie 100 and the bone tie advancer 200 can have any shape that allows the passage through the first lumen 400 and into the second lumen 402.

The bone tie 100 is advanced until the head 136 of bone tie 100 is positioned near the bone tie retriever 300. The bone tie 100 is advanced until the head 136 of bone tie 100 is inserted into the channel 316. The bone tie 100 and the bone tie advancer 200 can have any shape that allows the passage of the head 136 into the channel 316. The bone tie 100 can be advanced until the head 136 abuts the inside wall of the retriever portion 314. The bone tie 100 can be advanced until any further advancement is prevented by the retriever portion 314.

During advancement, the head 136 of the bone tie 100 can be monitored under radiographic visualization. The head 136 can include one or more markers 144. In the illustrated embodiment, the head 136 can include a bore 146 configured to receive the marker 144. The marker 144 can facilitate visualization of the head 136 because the marker 144 can be radiopaque. The marker 144 can facilitate placement of the head 136 relative to the lumens 400, 402. The marker 144 can facilitate placement of the head 136 relative to the retriever portion 314.

Figure 17:
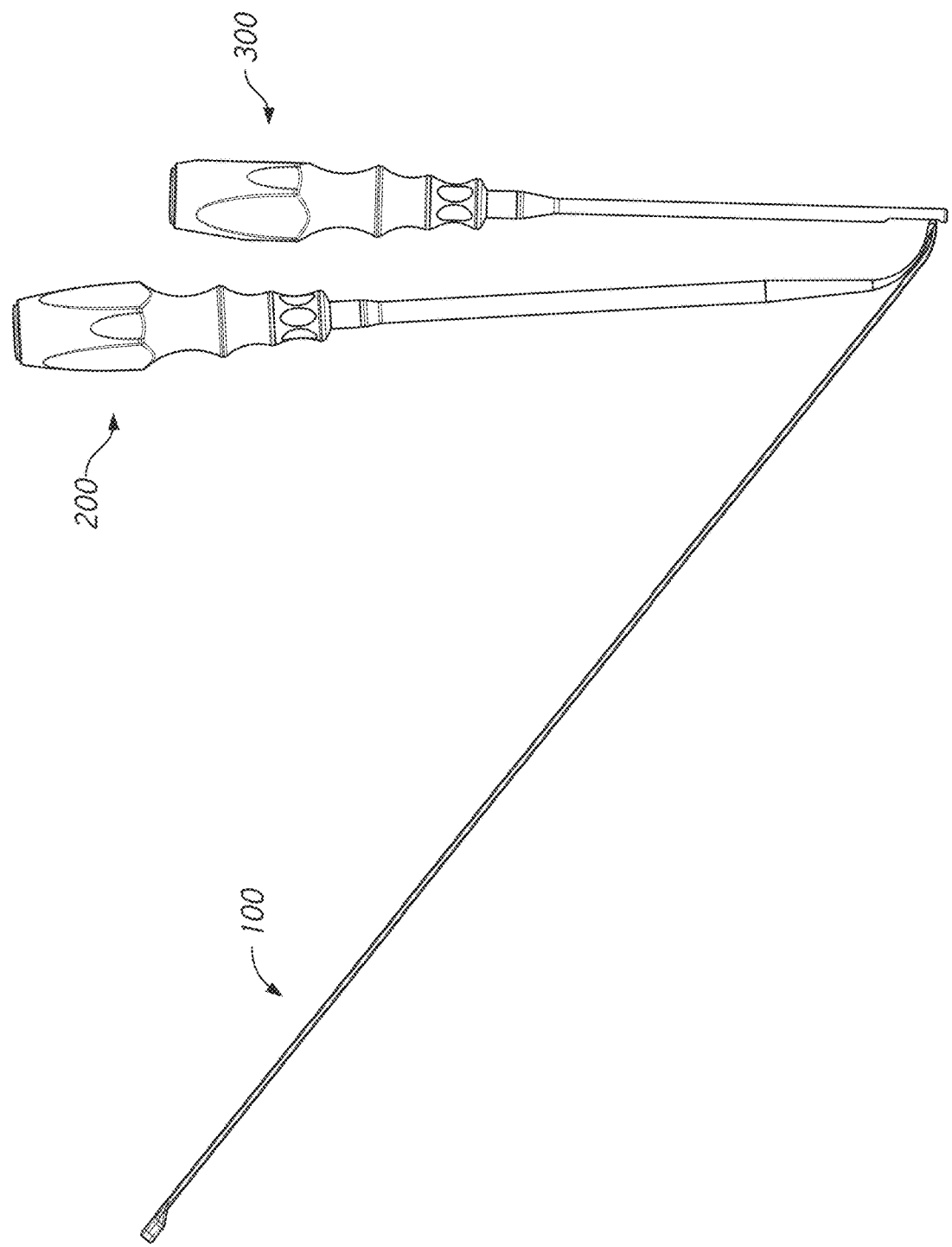
FIG. 17 is a side view of the bone tie of FIG. 1, the bone tie advancer of FIG. 6, and the bone tie retriever of FIG. 9.
Figure 18:
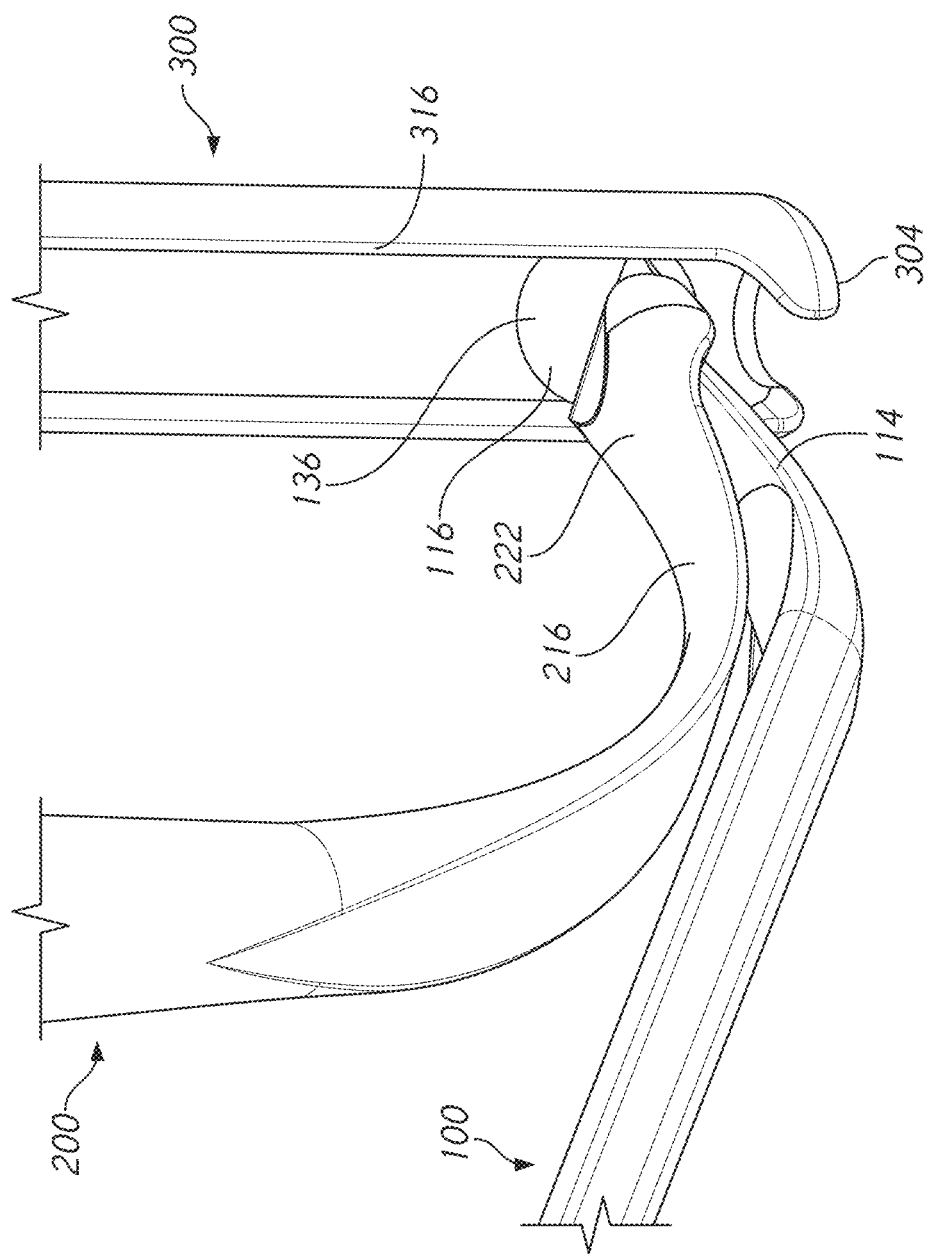
FIG. 18 is a perspective view of the bone tie of FIG. 1, the bone tie advancer of FIG. 6, and the bone tie retriever of FIG. 9.

FIGS. 17-18 illustrate the bone tie 100, the bone tie advancer 200, and the bone tie retriever 300 during methods of use. FIG. 17 is a side view of the bone tie 100, the bone tie advancer 200, and the bone tie retriever 300. FIG. 18 is a perspective view of the bone tie 100, the bone tie advancer 200, and the bone tie retriever 300.

The bone tie 100 can be coupled to the bone tie advancer 200. FIG. 17 illustrates the bone tie 100 coupled to the bone tie advancer 200. FIG. 18 is an enlarged view of the distal portion. The bone tie 100 can include the neck section 114 and the head section 116. The bone tie advancer 200 can include the advancer portion 222. The advancer portion 222 can couple to the head section 116 of the bone tie 100. The advancer portion 222 can couple to the head 136 of the bone tie 100. The advancer portion 222 can include a curved surface 224 that can grasp the head 136. The advancer portion 222 can couple to the neck section 114 of the bone tie 100. The advancer portion 222 can include a channel 228 that can grasp a portion of the neck section 114. The advancer portion 222 can couple to the bone tie 100 prior to insertion of the bone tie 100, or after bone tie 100 has been inserted, into a lumen in a bone portion. The movement of the bone tie advancer 200 can cause movement of the bone tie 100.

The bone tie advancer 200 can move the head 136 of the bone tie 100 toward the bone tie retriever 300. The retriever portion 314 can include the channel 316. The channel 316 can be concave along the longitudinal axis 350 of the shaft 310. The channel 316 can be shaped to receive the head 136 of the bone tie 100. The head 136 can be inserted proximal to the one or more retention features 324. The head 136 can be inserted along the length of the channel 316. The head 136 can be inserted proximal to the ledge 318. The head 136 can be inserted proximal to the opening 322.

The head 136 enters the channel 316 when advanced by the bone tie advancer 200. The neck section 114 enters the channel 316 when advanced by the bone tie advancer 200. In some methods of use, the bone tie advancer 200 enters the channel 316. In some methods of use, the bone tie advancer 200 does not enter the channel 316.

The bone tie advancer 200 can be used to advance the bone tie 100 through the first lumen 400. The first lumen 400 can be curved. The bone tie advancer 200 can include the curved portion 216. The curved portion 216 can have the same or similar curvatures as the curved lumen 400. The curved lumen 400 can be formed in the bone to allow passage of the bone tie advancer 200. The user manipulates the proximal handle 206 to align the advancer portion 222 with the opening of the first lumen 400. The user can pivot and/or rotate and translate the bone tie advancer 200 to move the bone tie advancer 200 and the bone tie 100 through the first vertebra V1. The user can pivot and/or rotate and translate the bone tie advancer 200 to move the bone tie advancer 200 and the bone tie 100 through the facet joint space. The user can pivot and/or rotate and translate the bone tie advancer 200 to move the bone tie advancer 200 and the bone tie 100 into the second vertebra V2.

The bone tie retriever 300 can be inserted into the second lumen 402. The second lumen 402 can be generally straight. The second lumen 402 can extend distally beyond the first lumen 400. The second lumen 402 can extend to a depth to allow the channel 316 of the bone tie retriever 300 to align with the first lumen 400 when the bone tie retriever 300 is within the second lumen 402. The second lumen 402 can be any size or depth in order to accommodate the retriever portion 314 therewithin. The retriever portion 314 can be positioned within the second lumen 402 such that when the head section 116 is advanced from the first lumen 400, the head section 116 is inserted along the length of the channel 316. In some embodiments, the retriever portion 314 can be positioned within the second lumen 402 such that when the head section 116 is advanced from the first lumen 400, the head section 116, or the head section 116 and at least a portion of the neck section 114, is inserted along the length of the channel 316. The retriever portion 314 can be positioned such that the head 136 is inserted proximal to the one or more retention features 324. In some embodiments, the distal end 304 of the bone tie retriever 300 can be recessed below the first lumen 400 when the bone tie retriever 300 is received within the second lumen 402.

Figure 19:
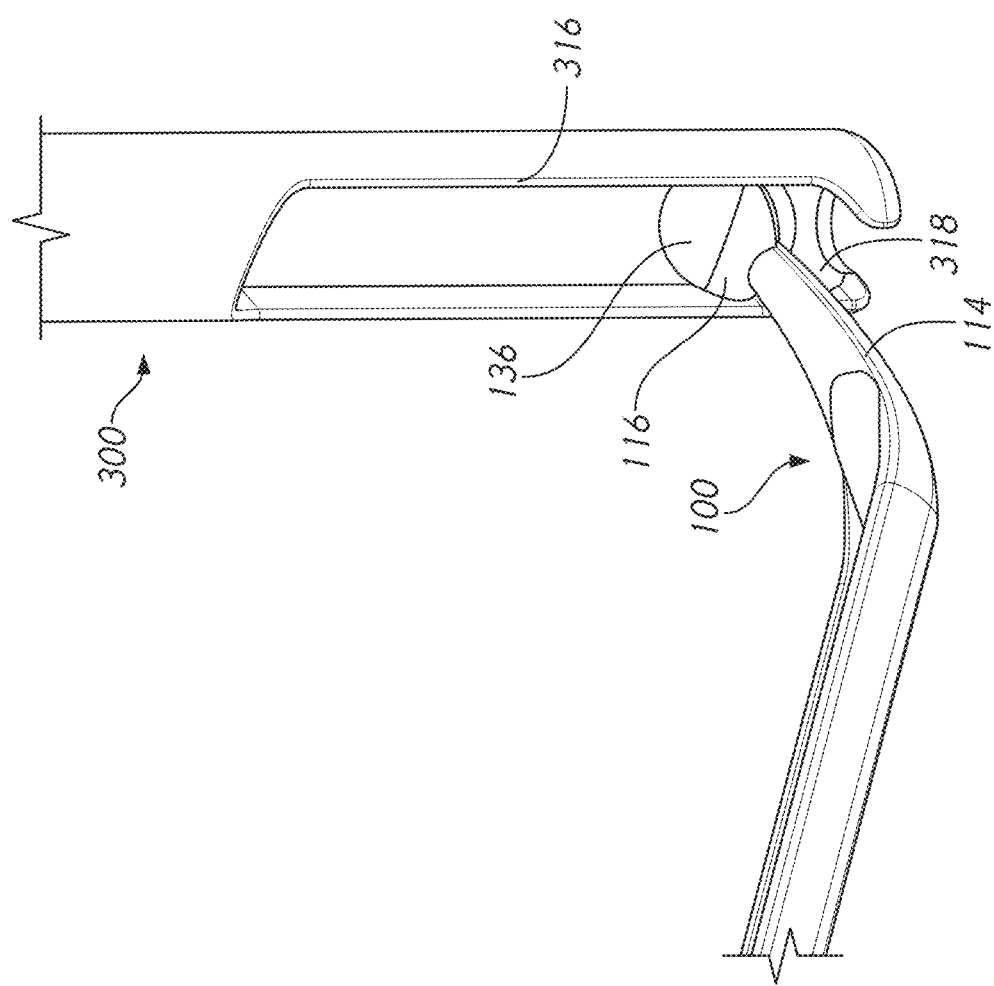
FIG. 19 is a perspective view of the bone tie of FIG. 1 and the bone tie retriever of FIG. 9.
Figure 20:
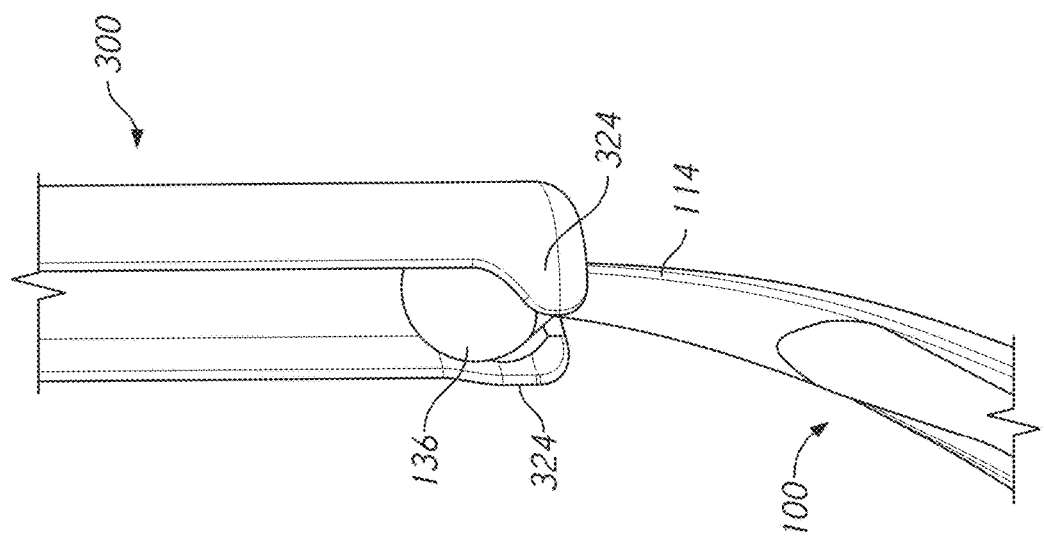
FIG. 20 is a perspective view of the bone tie of FIG. 1 and the bone tie retriever of FIG. 9.
Figure 21:
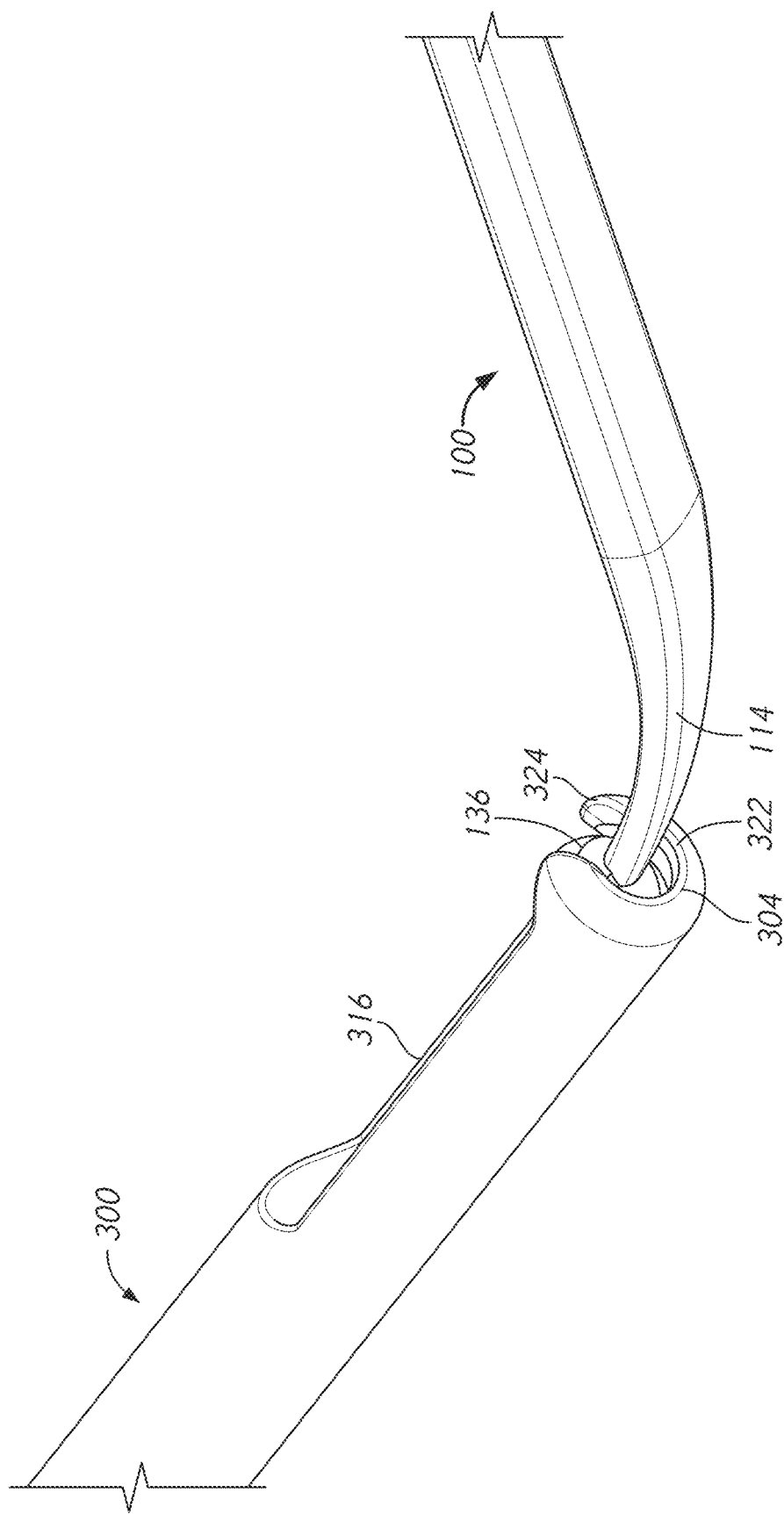
FIG. 21 is a distal view of the bone tie of FIG. 1 and the bone tie retriever of FIG. 9.

FIGS. 19-21 illustrate the bone tie 100 and the bone tie retriever 300 during methods of use. FIG. 19 is a perspective view of the bone tie 100 and the bone tie retriever 300 in a first orientation. FIG. 20 is a perspective view of the bone tie 100 and the bone tie retriever 300 in a second orientation. FIG. 21 is a distal view of the bone tie 100 and the bone tie retriever 300 in the second orientation.

FIG. 19 is a perspective view of the bone tie 100 and the bone tie retriever 300 in a first orientation. In some methods of use, the head 136 of the bone tie 100 is inserted into the bone tie retriever 300 in generally one particular orientation. In some methods of use, the neck section 114 of the bone tie 100 is perpendicular to the longitudinal axis 350 of the bone tie retriever 300 when the bone tie 100 is inserted into the bone tie retriever 300. In some methods of use, the head 136 of the bone tie 100 is inserted into the bone tie retriever 300 in a range of orientations. In some methods of use, the neck section 114 of the bone tie 100 is generally skewed to the longitudinal axis 350 of the bone tie retriever 300 when the bone tie 100 is inserted into the bone tie retriever 300. In some methods of use, the neck section 114 of the bone tie 100 can be any angle to the longitudinal axis 350 of the bone tie retriever 300 including 10°, 20°, 30°, 40°, 50°, 60°, 70°, 80°, 90°, 100°, 110°, 120°, 130°, 140°, 150°, 160°, 170°, 180°, or any range of the foregoing values. In particular methods of use, the neck section 114 of the bone tie 100 can be any angle to the longitudinal axis 350 of the bone tie retriever 300 including 60°, 70°, 80°, 90°, 100°, 110°, 120°, or any range of the foregoing values.

FIG. 20 is a perspective view of the bone tie 100 and the bone tie retriever 300 in a second orientation. FIG. 21 is a distal view of the bone tie 100 and the bone tie retriever 300 in the second orientation. In some methods of use, the neck section 114 of the bone tie 100 is generally aligned with the longitudinal axis 350 of the bone tie retriever 300 when the bone tie 100 is pivoted. In some methods of use, the neck section 114 of the bone tie 100 can be any angle to the longitudinal axis 350 of the bone tie retriever 300 including 0°, 5°, 10°, 15°, 20°, 25°, 30°, 35°, 40°, 45°, 50°, 55°, 60°, or any range of the foregoing values.

In some methods of use, the head 136 of the bone tie 100 is configured to slide within the channel 316. In some methods of use, the head 136 slides distally within the channel 316. The channel 316 can include the ledge 318. The ledge 318 can include a curvature that corresponds to the curvature of the head 136. The ledge 318 can be dimensioned to allow for pivotal and/or rotational movement of the head 136 within the channel 316. In some embodiments, the ledge 318 can have a curved or poly-axial surface configured to accept the head 136. In some embodiments, the ledge 318 can be concave. In some embodiments, the ledge 318 can have a concavity that corresponds to a convexity of the head 136. The ledge 318 can allow the head 136 to abut and rotate against the ledge 318. The one or more retention features 324 can allow the head 136 to be seated and rotate within the distal portion of the bone tie retriever 300. As the head 136 slides distally, the neck section 114 slides between the one or more retention features 324.

The concavity of the ledge 318 can allow the head 136 to pivot and/or rotate while still retaining the head 136 within the channel 316. The ledge 318 can allow the head 136, and thus the bone tie 100, to pivot and/or rotate. In some methods of use, the bone tie 100 can pivot approximately 90°. In some methods of use, the bone tie 100 pivots 30°, 40°, 50°, 60°, 70°, 80°, 90°, 100°, 110°, 120°, 130°, 140°, 150°, or any range of the foregoing values.

In some embodiments, the channel 316 may be dimensioned to allow retention of the head 136 when the neck section 114 is generally parallel or coaxial to the longitudinal axis 350 of the shaft 310. In some embodiments, the channel 316 is configured to allow the neck section 114 to pass between the one or more retention features 324. In some embodiments, the retriever portion 314 is configured to allow the neck section 114 to pivot, or pivot and rotate, from extending between the one or more retention features 324 into the opening 322. The opening 322 can be located at or near the distal end 304. The ledge 318 surrounds the opening 322. The ledge 318 can be shaped to support the head 136 when the bone tie 100 is pivoted and/or rotated. The ledge 318 and/or the one or more retention features 324 can be shaped to constrain the head 136 when the bone tie 100 is pivoted and/or rotated.

The bone tie 100 can be retracted by the bone tie retriever 300. The bone tie retriever 300 can be pulled distally from the second lumen 402. The neck section 114 can pivot and/or rotate to extend distally from the bone tie retriever 300 as the bone tie 100 is pulled proximally. The one or more retention features 324 can limit or prevent lateral movement of the head 136 when the bone tie is in the second orientation relative to the bone tie retriever 300. The one or more retention features 324 can facilitate retention of the head 136 within the channel 316. The bone tie retriever 300 can pull the bone tie 100 through the second lumen 402. The bone tie retriever 300 can pull the bone tie 100 until the distal end 104 of the bone tie 100 is outside of the lumen 402.

In some methods of use, the proximal end 102 and the distal end 104 can be outside of the vertebrae after use of the bone tie advancer 200 and bone tie retriever 300. The bone tie 100 can form a curved shape. In some methods of use, a portion of the second section 110 can be disposed within the lumens 400, 402. In some methods of use, a portion of the third section 112 can be disposed within the lumens 400, 402. In some methods of use, a portion of the second section 110 and a portion of the third section 112 can be disposed within the lumens 400, 402 when the proximal end 102 and the distal end 104 are outside of the vertebrae.

In some methods of use, the head section 116 can be removed. The bone tie 100 can be cut or severed near the neck section 114. The bone tie 100 can be cut or severed to remove the head section 116. The bone tie 100 can be cut or severed to remove the head section 116 and a portion of the neck section 114. The head section 116 can be discarded. The head section 116 and a portion of the neck section 114 can be discarded. The neck section 114 can be advanced through the lumen 118 of the fastener section 106. While the neck 114 is being advanced, the ratchet 122 can extend into the groove 132. The third section 112 can be advanced through the lumen 118. While the third section 112 is being advanced, the ratchet 122 can extend into the groove 130. The second section 110 can be advanced through the lumen 118. While the second section 110 is being advanced, the ratchet 122 can extend into the groove 126. The ratchet 122 can engage the one or more gears 128. The ratchet 122 can allow the second section 110 to travel through the lumen 118 in one direction, but limit or prevent travel in the opposite direction.

The bone tie 100 can form a loop. The fastener section 106 can be secured to the second section 110. Securing the fastener section 106 can be based on the type of fastener member used. By way of example, securing the fastener section 106 can include inserting the opposite end of the bone tie 100 into the lumen 118 of the fastener section 106, and advancing the opposite end through the fastener section 106. The fastener section 106 can engage the one or more gears 128 of the second section 110. The one or more gears 128 can be shaped to allow each gear 128 to displace the ratchet 122 of fastener section 106 in only one direction.

After the bone tie 100 is secured, superior articular process SAP of vertebra V2 can fuse to inferior articular process IAP of vertebra V1. Fusing can include one or more of bone material from superior articular process SAP of vertebra V2, bone material from inferior articular process IAP of vertebra V1, and/or the implant or prosthesis that fuses articular process SAP of vertebra V2 to inferior articular process IAP of vertebra V1. In some embodiments, after superior articular process SAP of vertebra V2 is fused to inferior articular process IAP of vertebra V1, the bone tie 100 is not removed. In some embodiments, after superior articular process SAP of vertebra V2 is fused to inferior articular process IAP of vertebra V1, all or a portion of the bone tie 100 can be removed. In some embodiments, the bone tie 100 can be removed after fusion of superior articular process SAP of vertebra V2 to inferior articular process IAP of vertebra V1 has started, but has not finished. In some embodiments, the bone tie 100 may comprise a bioabsorbable or bioresorbable material.

In use, the bone tie 100 can be configured to stabilize a first vertebra and/or a second vertebra by securing an articular process of the first vertebra to an articular process of a second vertebra. More specifically, the bone tie 100 can be configured to stabilize the first vertebra and/or a second vertebra by securing an articular process of the first vertebra to an articular process of a second vertebra. The bone tie 100 can be placed into a suitable position relative to the first vertebra and/or the second vertebra, and a distal portion of the bone tie 100 can be inserted into the lumen of the fastener section 106. The bone tie 100 can be configured to substantially encircle at least a portion of the first vertebra and the second vertebra. In some methods of use, the bone tie 100 forms a loop about the articular process of the first vertebra and the articular process of the second vertebra. In some methods of use, the neck section 114 and the third section 112 can be advanced through the fastener section 106 such that the area disposed within the loop formed by the bone tie 100 is reduced.

As the bone tie 100 is tightened, the bone tie 100 exerts a compressive force on the articular process of the first vertebra and the articular process of the second vertebra. In some methods of use, the implant or prosthesis can be disposed between the articular process of the first vertebra and the articular process of the second process such that a desired distance between the articular process of the first vertebra and the articular process of the second process is maintained. The implant or prosthesis can be retained within a loop or other defined segment of the bone tie 100. In some methods of use, the excess portion of the second section 110 and/or the third section 112 can be removed once the bone tie 100 is tightened. In some embodiments, the excess portion of the bone tie 100 can be removed from the space around the vertebrae. The excess portion of the bone tie 100 can be removed by cutting or breaking the excess portion of the bone tie 100. The excess portion can be removed without loosening or removing the loop formed by the bone tie 100 around the first vertebra and the second vertebra.

In some embodiments described herein, the bone tie 100 can be used to stabilize and/or fixate a first vertebra to a second vertebra. The bone tie 100 can be configured to reduce pain associated with a bone portion. The bone tie 100 can be configured to reduce further degradation of a spine. The bone tie 100 can be configured to reduce further degradation of a specific vertebra of a spine. The bone tie 100 can be configured to reduce movement until the first vertebra and the second vertebra have fused. The bone tie 100 can be configured to stabilize the first vertebra and second vertebra by securing an articular process of the first vertebra to an articular process of a second vertebra.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A bone tie inserter, comprising:
    a bone tie comprising:
        a proximal end and a distal end;
        a head section comprising a rounded, spherical head; and
        a body section comprising one or more gears;
    a bone tie advancer comprising:
        a bone tie advancer shaft; and
        an advancer portion comprising a curved surface configured to guide the rounded, spherical head of the bone tie;
    a bone tie retriever comprising:
        a bone tie retriever shaft; and
        a retriever portion configured to receive the rounded, spherical head of the bone tie, wherein the rounded, spherical head of the bone tie is configured to pivot and/or rotate within the retriever portion.

2. The bone tie inserter of claim 1, wherein the body section of the bone tie comprises a groove.

3. The bone tie inserter of claim 1, wherein the head section of the bone tie comprises a flange.

4. The bone tie inserter of claim 1, wherein the head section of the bone tie comprises a radiopaque marker.

5. The bone tie inserter of claim 1, wherein the advancer portion comprises a curve.

6. The bone tie inserter of claim 1, wherein the retriever portion comprises a ledge.

7. The bone tie inserter of claim 1, wherein the retriever portion comprises a channel.

8. The bone tie inserter of claim 1, wherein the advancer portion comprises a channel configured to receive a neck section extending proximally from the rounded, spherical head.

9. The bone tie inserter of claim 1, wherein the bone tie further comprises a fastener section, wherein the fastener section comprises a ratchet.

10. A method of treating bone portions, the method comprising:
    forming a lumen in a first bone portion;
    forming a lumen in a second bone portion;
    advancing a rounded, spherical head of a bone tie with a bone tie advancer through the lumen of the first bone portion and into the lumen of the second bone portion, wherein the bone tie advancer is removably coupled to the rounded, spherical head or a neck section extending from the rounded, spherical head, wherein the bone tie comprises a body section comprising one or more gears;
    advancing the rounded, spherical head of the bone tie into a retriever portion of a bone tie retriever, the retriever portion comprising a channel to receive the rounded, spherical head; and
    withdrawing the bone tie retriever from the second bone portion, wherein the bone tie is configured to pivot and/or rotate as the bone tie retriever is withdrawn.

11. The method of claim 10, wherein the bone tie advancer comprises a channel to receive the neck section of the bone tie.

12. The method of claim 10, wherein the bone tie advancer comprises a curve.

13. The method of claim 10, wherein the bone tie advancer comprises a rounded section to abut the rounded, spherical head of the bone tie.

14. The method of claim 10, wherein the bone tie retriever comprises an opening, wherein the neck section pivots, or pivots and rotates, from extending from the channel to extending through the opening.

15. The method of claim 10, wherein the bone tie retriever comprises one or more retention features configured to retain the bone tie.

16. The method of claim 10, wherein the bone tie retriever comprises a ledge.

17. The method of claim 16, wherein the ledge facilitates pivoting and/or rotating of the rounded, spherical head of the bone tie.

18. The method of claim 10, wherein the bone tie further comprises a fastener section, wherein the fastener section comprises a ratchet.

* * * * *